United States Patent
Magnusson et al.

(10) Patent No.: US 7,781,424 B2
(45) Date of Patent: *Aug. 24, 2010

(54) MODIFIED RELEASE PHARMACEUTICAL FORMULATION

(75) Inventors: Anders Magnusson, Mölndal (SE); Mikael Thune, Mölndal (SE)

(73) Assignee: AstraZeneca AB, Sodertalje (SE)

( * ) Notice: Subject to any disclaimer, the term of this patent is extended or adjusted under 35 U.S.C. 154(b) by 522 days.

This patent is subject to a terminal disclaimer.

(21) Appl. No.: 11/716,021

(22) Filed: Mar. 9, 2007

(65) Prior Publication Data

US 2008/0050437 A1    Feb. 28, 2008

Related U.S. Application Data

(63) Continuation of application No. 10/516,420, filed as application No. PCT/SE03/00858 on May 27, 2003, now Pat. No. 7,202,236.

(51) Int. Cl.
*A61K 3/397*    (2006.01)

(52) U.S. Cl. .............................. 514/210.02; 514/210.7; 548/952; 548/953

(58) Field of Classification Search ........................ None
See application file for complete search history.

(56) References Cited

U.S. PATENT DOCUMENTS

| | | | |
|---|---|---|---|
| 4,346,078 A | 8/1982 | Bajusz et al. ................. 514/19 |
| 4,703,036 A | 10/1987 | Bajusz et al. |
| 4,792,452 A | 12/1988 | Howard et al. .............. 424/475 |
| 5,053,416 A | 10/1991 | Toja et al. |
| 5,260,307 A | 11/1993 | Ackermann et al. |
| 5,393,760 A | 2/1995 | Ackermann et al. |
| 5,405,854 A | 4/1995 | Ackermann et al. |
| 5,498,724 A | 3/1996 | Nystrom et al. .......... 548/375.1 |
| 5,532,232 A | 7/1996 | Ackermann et al. |
| 5,559,232 A | 9/1996 | Ackermann et al. ......... 544/121 |
| 5,578,594 A | 11/1996 | Ackermann et al. |
| 5,583,133 A | 12/1996 | Ackermann et al. |
| 5,595,999 A | 1/1997 | Ackermann et al. |
| 5,602,253 A | 2/1997 | Antonsson et al. ......... 544/330 |
| 5,659,071 A | 8/1997 | Nystrom et al. ............. 560/159 |
| 5,677,448 A | 10/1997 | Ackermann et al. |
| 5,705,487 A | 1/1998 | Schacht et al. ................. 514/19 |
| 5,707,966 A | 1/1998 | Schacht et al. ................. 514/19 |
| 5,710,130 A | 1/1998 | Schacht et al. ................. 514/19 |
| 5,723,444 A | 3/1998 | Antonsson et al. ........... 514/19 |
| 5,744,487 A | 4/1998 | Ohshima et al. ............ 514/326 |
| 5,763,436 A | 6/1998 | Ackermann et al. |
| 5,763,604 A | 6/1998 | Ackermann et al. |
| 5,780,631 A | 7/1998 | Antonsson et al. ............. 546/1 |
| 5,783,563 A | 7/1998 | Antonsson et al. ............ 514/19 |
| 5,856,307 A | 1/1999 | Antonsson et al. ............ 514/18 |
| 5,939,392 A | 8/1999 | Antonsson et al. ............ 514/18 |
| 5,965,692 A | 10/1999 | Gustafsson et al. ......... 530/300 |
| 6,030,972 A | 2/2000 | Bohm et al. ................. 514/257 |
| 6,034,104 A | 3/2000 | Klimkowski et al. |
| 6,051,568 A | 4/2000 | Gustafsson et al. .... 514/210.17 |
| 6,083,532 A | 7/2000 | Zhang et al. |
| 6,221,898 B1 | 4/2001 | Antonsson ................. 514/445 |
| 6,225,287 B1 | 5/2001 | Edvardsson et al. .......... 514/19 |
| 6,255,301 B1 | 7/2001 | Gustafsson et al. |
| 6,262,028 B1 | 7/2001 | Antonsson et al. ............ 514/19 |
| 6,265,397 B1 | 7/2001 | Karlsson et al. ........ 514/210.17 |
| 6,287,599 B1 | 9/2001 | Burnside et al. |
| 6,337,343 B1 | 1/2002 | Gustafsson et al. |
| 6,337,346 B1 | 1/2002 | Lee et al. |
| 6,337,394 B2 | 1/2002 | Karlsson et al. |
| 6,433,186 B1 | 8/2002 | Inghardt et al. |
| 6,440,937 B1 | 8/2002 | Baucke et al. ................. 514/19 |
| 6,440,939 B2 | 8/2002 | Edvardsson et al. .......... 514/19 |
| 6,444,817 B1 | 9/2002 | Bohm et al. ................. 544/334 |
| 6,455,671 B1 | 9/2002 | Bohm et al. ................. 530/331 |
| 6,479,078 B1 | 11/2002 | Hedstrom et al. ........... 424/489 |
| 6,521,253 B1 | 2/2003 | Forsman et al. ............. 424/464 |
| 6,576,245 B1 | 6/2003 | Lundgren et al. ........... 424/400 |

(Continued)

FOREIGN PATENT DOCUMENTS

EP          0185390          10/1991

(Continued)

OTHER PUBLICATIONS

Gupta et al. "Controlled-release tablets from carrageenans: effect of formulation, storage and dissolution factors" Eur. J. Pharm. Biopharm., 51(3):241-248 (2001).

(Continued)

*Primary Examiner*—Eric E. Silverman
(74) *Attorney, Agent, or Firm*—Morgan Lewis & Bockius LLP

(57) ABSTRACT

A modified release pharmaceutical composition comprising, as active ingredient, a compound of formula (I), wherein $R_1$ represents $C_{1-2}$ alkyl substituted by one or more fluoro substituents; $R_2$ represents hydrogen, hydroxy, methoxy or ethoxy, and n represents 0, 1 or 2; or a pharmaceutically acceptable salt thereof; and a pharmaceutically acceptable diluent or carrier; provided that the formulation may only contain iota-carageenan and a neutral gelling polymer when the compound of formula (I) is in the form of a salt; such formulations being of use for the treatment of a cardiovascular disorder.

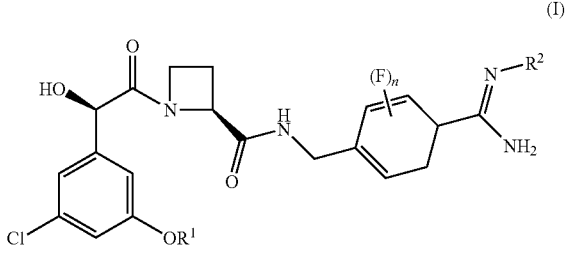

(I)

5 Claims, No Drawings

U.S. PATENT DOCUMENTS

| | | | |
|---|---|---|---|
| 6,576,657 B2 | 6/2003 | Karlsson et al. | 514/423 |
| 6,599,894 B1 | 7/2003 | Inghardt et al. | 514/210.02 |
| 6,617,320 B2 | 9/2003 | Gustafsson et al. | |
| 6,660,279 B2 | 12/2003 | Lundgren et al. | 424/400 |
| 6,716,834 B2 | 4/2004 | Andersson et al. | 514/210.02 |
| 6,750,243 B1 | 6/2004 | Inghardt et al. | 514/422 |
| 6,811,794 B2 | 11/2004 | Burnside et al. | |
| 6,838,478 B2 | 1/2005 | Gustafsson et al. | |
| 6,875,446 B2 | 4/2005 | Forsman et al. | 424/464 |
| 6,888,007 B2 | 5/2005 | Edvardsson et al. | 548/953 |
| 6,921,758 B2 | 7/2005 | Gustafsson et al. | 514/210.17 |
| 6,984,627 B1 | 1/2006 | Antonsson et al. | 514/19 |
| 6,998,136 B2 | 2/2006 | Lundgren et al. | 424/422 |
| 7,056,907 B2 | 6/2006 | Inghardt et al. | 514/210.02 |
| 7,129,233 B2 | 10/2006 | Inghardt et al. | |
| 7,202,236 B2 | 4/2007 | Magnusson et al. | |
| 7,273,858 B2 | 9/2007 | Ahlqvist et al. | |
| 2003/0004308 A1 | 1/2003 | Bohm et al. | |
| 2004/0019033 A1 | 1/2004 | Inghardt et al. | 514/210.17 |
| 2004/0242492 A1 | 12/2004 | Inghardt et al. | 514/19 |
| 2004/0242536 A1 | 12/2004 | Khoo et al. | |
| 2005/0171083 A1 | 8/2005 | Magnusson et al. | |
| 2006/0014734 A1 | 1/2006 | Alami et al. | |
| 2006/0111553 A1 | 5/2006 | Boehm et al. | |
| 2007/0202174 A1 | 8/2007 | Inghardt et al. | |
| 2007/0218136 A1 | 9/2007 | Inghardt et al. | |
| 2008/0090800 A1 | 4/2008 | Inghardt et al. | |
| 2008/0269176 A1 | 10/2008 | Ahlqvist et al. | |
| 2008/0287413 A1 | 11/2008 | Ymen et al. | |
| 2008/0293965 A1 | 11/2008 | Bosson | |
| 2008/0312457 A1 | 12/2008 | Blixt et al. | |
| 2008/0319206 A1 | 12/2008 | Al-Saffar et al. | |

FOREIGN PATENT DOCUMENTS

| | | |
|---|---|---|
| EP | 0526877 | 2/1993 |
| EP | 0293881 | 3/1993 |
| EP | 0530167 | 3/1993 |
| EP | 0539059 | 4/1993 |
| EP | 0195212 | 11/1993 |
| EP | 0468231 | 9/1994 |
| EP | 0641779 | 3/1995 |
| EP | 0648780 | 4/1995 |
| EP | 0362002 | 7/1995 |
| EP | 0686642 | 12/1995 |
| EP | 0364344 | 5/1998 |
| EP | 0542525 | 7/1998 |
| EP | 0559046 | 7/2001 |
| EP | 0669317 | 9/2002 |
| EP | 0773955 | 4/2003 |
| EP | 0672658 | 9/2003 |
| JP | 57149217 | 9/1982 |
| WO | WO 93/11152 | 6/1993 |
| WO | WO 93/18060 | 9/1993 |
| WO | WO 94/29269 | 12/1994 |
| WO | WO 94/29336 | 12/1994 |
| WO | WO 95/23609 | 9/1995 |
| WO | WO 95/35309 | 12/1995 |
| WO | WO 96/03374 | 2/1996 |
| WO | WO 96/25426 | 8/1996 |
| WO | WO 96/26717 | 9/1996 |
| WO | WO 96/31504 | 10/1996 |
| WO | WO 96/32110 | 10/1996 |
| WO | WO 97/02284 | 1/1997 |
| WO | WO 97/23499 | 7/1997 |
| WO | WO 97/39770 | 10/1997 |
| WO | WO 97/46577 | 12/1997 |
| WO | WO 97/49404 | 12/1997 |
| WO | WO 98/01422 | 1/1998 |
| WO | WO 98/06740 | 2/1998 |
| WO | WO 98/16252 | 4/1998 |
| WO | WO 98/57932 | 12/1998 |
| WO | WO 99/21586 | 5/1999 |
| WO | WO 99/27913 | 6/1999 |
| WO | WO 99/29305 | 6/1999 |
| WO | WO 99/29664 | 6/1999 |
| WO | WO 99/39698 | 8/1999 |
| WO | WO 00/12043 | 3/2000 |
| WO | WO 00/13671 | 3/2000 |
| WO | WO 00/13710 | 3/2000 |
| WO | WO 00/14110 | 3/2000 |
| WO | WO 00/18352 | 4/2000 |
| WO | WO 00/35869 | 6/2000 |
| WO | WO 00/42059 | 7/2000 |
| WO | WO 01/02426 | 1/2001 |
| WO | WO 01/87879 | 11/2001 |
| WO | WO 02/14270 | 2/2002 |
| WO | WO 02/19990 | 3/2002 |
| WO | WO 02/44145 | 6/2002 |
| WO | WO 03/000293 | 1/2003 |
| WO | WO 03/018551 | 3/2003 |
| WO | WO 03/090723 | 11/2003 |
| WO | WO 03/101423 | 12/2003 |
| WO | WO 03/101424 | 12/2003 |
| WO | WO 03/101957 | 12/2003 |
| WO | WO 2005/054168 | 6/2005 |
| WO | WO 2006/090153 | 8/2006 |
| WO | WO 2006/125964 | 11/2006 |
| WO | WO 2008/068475 | 6/2008 |

OTHER PUBLICATIONS

Talukdar et al. "Comparative study on xanthan gum and hydroxypropylmethyl cellulose as matrices for controlled-release drug delivery I. Compaction and in vitro drug release behaviour" International Journal of Pharmaceutics, 129(2):233-241 (1996).

Berge et al. "Pharmaceutical Salts" J. of Pharmaceutical Sciences 66(1):1-19 (1977).

CAS RN 30318-53-4 Nov. 2000.

CAS RN 192939-72-3 Aug. 1997.

CAS RN 159776-70-2 Dec. 1994.

Baveja et al. "Zero-order release hydrophilic matrix tablets of beta-adrenergic blockers" International Journal of Pharmaceutics 39:39-45 (1987).

Bonferoni et al. "On the employment of lambda-carrageenan in a matrix system. II. Lambda-Carrageenan and hydroxypropylmethylcellulose mixtures" J. Controlled Release 30:175-182 (1994).

Ham-Yong Park et al. "Effect of pH on Drug Release From Polysaccharide Tablets" Drug Delivery 5:13-18 (1998).

Picker "The use of carrageenan in mixture with microcrystalline cellulose and its functionality for making tablets" European J Pharmaceutics and Biopharmaceutics 48(1):27-36 (1999).

Talukdar et al. "In vivo evaluation of xanthan gum as a potential excipient for oral controlled-release matrix tablet formulation" International Journal of Pharmaceutics 169(1):105-113 (1998).

Deinum et al. "Biochemical and pharmacological effects of the direct thrombin inhibitor AR-H067637" Thromb Haemost. 101(6):1051-1059 (2009).

Eriksson et al. "Comparative pharmacodynamics and pharmacokinetics of oral direct thrombin and factor Xa inhibitors in development" Clinical Pharmacokinetics 48(1):1-22 (2009).

Gyzander et al. "Enzyme kinetic characterisation of the active form of the novel oral direct thrombin inhibitor AZD0837" Journal of Thrombosis and Haemostasis, 5 Supplement 2: P-S-066 (2007).

Hockings et al. "The oral direct thrombin inhibitor AZD0837 reduces thrombus formation in a rat model" Journal of Thrombosis and Haemostasis, 5 Supplement 2: P-S-697 (2007).

Lip et al. "The oral direct thrombin inhibitor AZD0837 for the prevention of stroke and systemic embolism in patients with atrial fibrillation: A phase II randomized dose-guiding, safety and tolerability study" Journal of the American College of Cardiology 53(10, Suppl. 1):A430 (2009).

Mattsson et al. "Characterisation of the active form of the novel oral direct thrombin inhibitor AZD0837 in coagulation assays" Journal of Thrombosis and Haemostasis, 5 Supplement 2: P-T-636 (2007).

Olsson et al. "Safety and tolerability of the oral direct thrombin inhibitor AZD0837 in prevention of stroke and other thromboembolic complications associated with atrial fibrillation (AF)" Journal of Thrombosis and Haemostasis, 5 Supplement 2: O-W-053 (2007).

Patani et al. "Bioisosterism: A rational approach in drug design" Chem. Rev. 96(8):3147-3176 (1996).

Pehrsson et al. "The antithrombotic effect of AR-H067637, the active form of the novel oral direct thrombin inhibitor AZD0837, in rat models of arterial and venous thrombosis" Journal of Thrombosis and Haemostasis, 5 Supplement 2 : P-W-637 (2007).

Schutzer et al. "Effect of the oral direct thrombin inhibitor AZD0837 on glomerular filtration rate in elderly healthy subjects" Journal of Thrombosis and Haemostasis, 5 Supplement 2: P-W-668 (2007).

Wagenvoord et al. "The effect of direct thrombin inhibitors (DTIS) in clotting plasma" Journal of Thrombosis and Haemostasis, 5 Supplement 2: P-W-654 (2007).

Walfridsson et al. "Assessment of the electrophysiological effects of the oral direct thrombin inhibitor AZD0837, in subjects undergoing an invasive electrophysiological procedure" Journal of Thrombosis and Haemostasis, 5 Supplement 2 : P-W-674 (2007).

MODIFIED RELEASE PHARMACEUTICAL FORMULATION

This is a continuation application of U.S. application Ser. No. 10/516,420 (filed Nov. 29, 2004), now U.S. Pat. No. 7,202,236 which is a U.S. National Phase Application of International Application No. PCT/SE03/00858 (filed May 27, 2003) which claims the benefit of Swedish Application No. 0201659-0 (filed May 31, 2002), all of which are hereby incorporated by reference in their Entirety.

This invention relates to novel modified release pharmaceutical formulations that provide for modified delivery of particular pharmaceuticals, to the manufacture of such formulations, and to the use of such a formulation in the treatment or prevention of thrombosis.

It is often necessary to administer pharmaceutically active compounds frequently throughout the day in order to maintain a desired therapeutic level of active principle in plasma, body tissues and/or the gastrointestinal tract. This is particularly the case where it is intended to deliver the drug orally and to provide a uniform response over an extended period of time.

Over the last thirty or so years, modified release dosage forms have increasingly become a preferred method of delivering certain drugs to patients, particularly via the oral route. Such forms may for example provide for release of drug over an extended period of time, thus reducing the number of required daily doses, and during which time the rate of release may be substantially uniform and/or constant, within a specific part of the gastrointestinal tract, or pulsative.

There are numerous modified release dosage forms known in the art and these have been summarised by inter alia De Haan and Lerk in *Pharmaceutisch Weekblad Scientific Edition*, 6, 57 (1984); Banker in "*Medical Applications of Controlled Release*", Vol II, eds. Langer and Wise (1984) Boca Raton, Fla., at pages 1 to 34; Graffner in *Industrial Aspects of Pharmaceuticals*, ed. Sandel, Swedish Pharmaceutical Press (1993) at pages 93 to 104; and Proudfoot "*Dosage Regimens: Their Influence on the Concentration-Time Profile of the Drug in the Body*" at pages 191 to 211 of "*Pharmaceutics: The Science of Dosage Form Design*", ed. M. E. Aulton (1988) (Churchill Livingstone).

International Patent Application No. PCT/SE01/02657 (WO 02/44145, earliest priority date 1 Dec. 2000, filed 30 Nov. 2001, published 6 Jun. 2002) discloses a number of compounds that are, or are metabolised to compounds which are, competitive inhibitors of trypsin-like proteases, such as thrombin. The following three compounds are amongst those that are specifically disclosed:

(a) Ph(3-Cl)(5-OCHF₂)—(R)CH(OH)C(O)—(S)Aze-Pab(OMe):

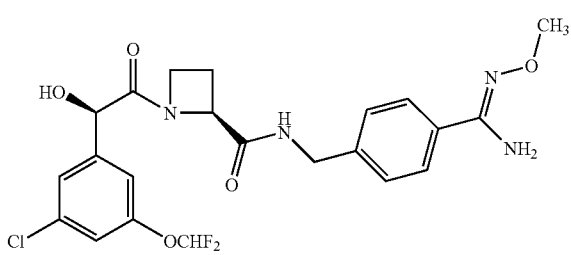

which compound is referred to hereinafter as Compound A;

(b) Ph(3-Cl)(5-OCHF₂)—(R)CH(OH)C(O)—(S)Aze-Pab(2,6-diF)(OMe):

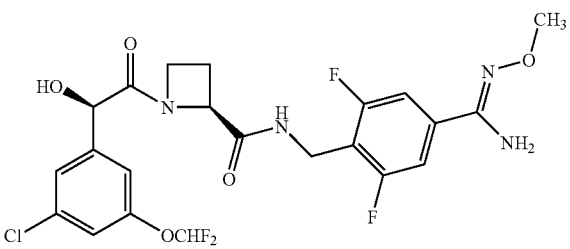

which compound is referred to hereinafter as Compound B; and (c) Ph(3-Cl)(5-OCH₂CH₂F)—(R)CH(OH)C(O)—(S)Aze-Pab(OMe):

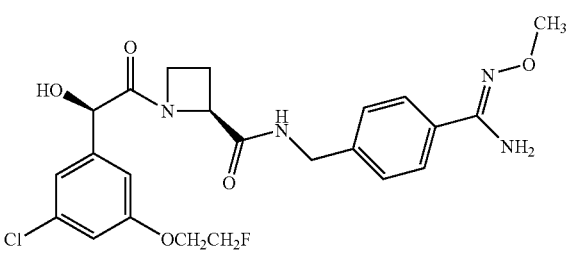

which compound is referred to hereinafter as Compound C.

The methoxyamidine Compounds A, B and C are metabolised following oral and/or parenteral administration to a mammal and form the corresponding free amidine compounds, which latter compounds have been found to be potent inhibitors of thrombin. Thus:

Compound A is metabolized to Ph(3-Cl)(5-OCHF₂)—(R)CH(OH)C(O)—(S)Aze-Pab (which compound is referred to hereinafter as Compound D) via a prodrug intermediate Ph(3-Cl)(5-OCHF₂)—(R)CH(OH)C(O)—(S)Aze-Pab(OH) (which compound is referred to hereinafter as Compound G);

Compound B is metabolized to Ph(3-Cl)(5-OCHF₂)—(R)CH(OH)C(O)—(S)Aze-Pab(2,6-diF) (which compound is referred to hereinafter as Compound E) via a prodrug intermediate Ph(3-Cl)(5-OCHF₂)—(R)CH(OH)C(O)—(S)Aze-Pab(2,6-diF)(OH) (which compound is referred to hereinafter as Compound H); and, Compound C is metabolized to Ph(3-Cl)(5-OCH₂CH₂F)—(R)CH(OH)C(O)—(S)Aze-Pab (which compound is referred to hereinafter as Compound F) via a prodrug intermediate Ph(3-Cl)(5-OCH₂CH₂F)—(R)CH(OH)C(O)—(S)Aze-Pab(OH) (which compound is referred to hereinafter as Compound J).

Processes for the synthesis of Compounds A, B, C, D, E, F, G and J are described in Examples 12, 40, 22, 3, 39, 21, 2 and 31 (respectively) of international patent application No. PCT/SE01/02657. A modified release formulation of these compounds, or their metabolites has yet to be described in the literature.

We have already found that Compounds A and C can be formulated in certain modified release iota-carrageenan formulations, and have now found that the compounds of formula (I) and their salts can be formulated in other modified release pharmaceutical formulations which are easy to administer, for example by oral administration.

According to a first aspect of the invention, there is provided a modified release pharmaceutical formulation comprising, as active ingredient, a compound of formula (I):

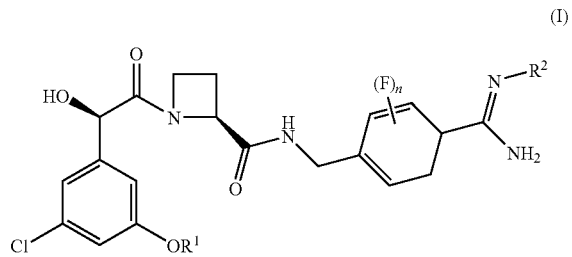

wherein
$R^1$ represents $C_{1-2}$ alkyl substituted by one or more fluoro substituents;
$R^2$ represents hydrogen, hydroxy, methoxy or ethoxy; and
n represents 0, 1 or 2;

or a pharmaceutically acceptable salt thereof; and a pharmaceutically acceptable diluent or carrier; provided that the formulation may only contain iota-carrageenan and a neutral gelling polymer when the compound of formula (I) is in the form of a salt; which formulations are referred to hereinafter as "the formulations of the invention".

The compounds of formula (I), or a pharmaceutically acceptable salt thereof, may be in the form of a solvate, a hydrate, a mixed solvate/hydrate or, preferably, an ansolvate, such as an anhydrate. Solvates may be of one or more organic solvents, such as lower (for example $C_{1-4}$) alkyl alcohols (for example methanol, ethanol or iso-propanol), ketones (such as acetone), esters (such as ethyl acetate) or mixtures thereof.

In one particular aspect of the invention $R^1$ is $CHF_2$ or $CH_2CH_2F$.

The variable n is preferably 0 or 2.

More preferred compounds of formula (I) include those in which n represents 0, or those in which n represents 2, so providing two fluoro atoms located at the 2- and 6-positions (that is the two ortho-positions relative to the point of attachment of the benzene ring to the —NH—CH₂— group).

The compound of formula (I) is especially Compound A, Compound B or Compound C.

A neutral gelling polymer is a single, or a mixture of more than one, neutral erodable polymer(s) having gelling properties and having substantially pH-independent solubility.

Preferred salts of the compounds of formula (I) are acid addition salts. Acid addition salts include inorganic acid addition salts, such as those of sulphuric acid, nitric acid, phosphoric acid and hydrohalic acids, such as hydrobromic acid and hydrochloric acid. More preferred acid addition salts include those of organic acids, such as those of dimethylphosphoric acid; saccharinic acid; cyclohexylsulfamic acid; those of carboxylic acids (such as maleic acid, fumaric acid, aspartic acid, succinic acid, malonic acid, acetic acid, benzoic acid, terephthalic acid, hippuric acid, 1-hydroxy-2-naphthoic acid, pamoic acid, hydroxybenzoic acid and the like); those of hydroxy acids (such as salicylic acid, tartaric acid, citric acid, malic acid (including L-(−)-malic acid and, D,L-malic acid), gluconic acid (including D-gluconic acid), glycolic acid, ascorbic acid, lactic acid and the like); those of amino acids (such as glutamic acid (including D-glutamic, L-glutamic, and D,L-glutamic, acids), arginine (including L-arginine), lysine (including L-lysine and L-lysine hydrochloride), glycine and the like); and, particularly, those of sulfonic acids, (such as 1,2-ethanedisulfonic acid, camphorsulfonic acids (including 1S-(+)-10-camphorsulfonic acid and (+/−)-camphorsulfonic acids), ethanesulfonic acid, a propanesulfonic acid (including n-propanesulfonic acid), a butanesulfonic acid, a pentanesulfonic acid, a toluenesulfonic acid, methanesulfonic acid, p-xylenesulfonic acid, 2-mesitylenesulfonic acid, naphthalenesulfonic acids (including 1,5-naphthalenesulfonic acid and naphthalenesulfonic acid), benzenesulfonic acid, hydroxybenzenesulfonic acids, 2-hydroxyethanesulfonic acid, 3-hydroxyethanesulfonic acid and the like).

Particularly preferred salts include those of $C_{1-6}$ (for example $C_{1-4}$) alkanesulfonic acids, such as ethanesulfonic acid (esylate) and propanesulfonic acid (for example n-propanesulfonic acid) and optionally substituted (for example with one or more $C_{1-2}$ alkyl groups) arylsulfonic acids, such as benzenesulfonic acid (besylate) and naphthalenedisulfonic acid.

Suitable stoichiometric ratios of acid to free base are in the range 0.25:1.5 to 3.0:1, such as 0.45:1.25 to 1.25:1, including 0.50:1 to 1:1.

According to a further aspect of the invention there is provided formulation comprising a compound of formula (I) in substantially crystalline form.

Although we have found that it is possible to produce compounds of the invention in forms which are greater than 80% crystalline, by "substantially crystalline" we include greater than 20%, preferably greater than 30%, and more preferably greater than 40% (e.g. greater than any of 50, 60, 70, 80 or 90%) crystalline.

According to a further aspect of the invention there is also provided a compound of the invention in partially crystalline form. By "partially crystalline" we include 5% or between 5% and 20% crystalline.

The degree (%) of crystallinity may be determined by the skilled person using X-ray powder diffraction (XRPD). Other techniques, such as solid state NMR, FT-IR, Raman spectroscopy, differential scanning calorimetry (DSC) and microcalorimetry, may also be used.

Preferred compounds of formula (I) that may be prepared in crystalline form include salts of $C_{1-6}$ (for example $C_{2-6}$, such as $C_{2-4}$) alkanesulfonic acids, such as ethanesulfonic acid, propanesulfonic acid (for example n-propanesulfonic acid) and optionally substituted arylsulfonic acids, such as benzenesulfonic acid and naphthalenedisulfonic acid.

The term "modified release" pharmaceutical composition will be well understood by the skilled person to include any composition/formulation in which the onset and/or rate of release of drug is altered by galenic manipulations, and thus includes the definition provided in the *United States Pharmacopeia* (USP XXII) at pages xliii and xliv of the preface/preamble part, the relevant disclosure in which document is hereby incorporated by reference.

In the present case, modified release may be provided for by way of an appropriate pharmaceutically-acceptable carrier, and/or other means, which carrier or means (as appropriate) gives rise to an alteration of the onset and/or rate of release of active ingredient. Thus, the term will be understood by those skilled in the art to include compositions which are adapted (for example as described herein) to provide for a "sustained", a "prolonged" or an "extended" release of drug (in which drug is released at a sufficiently retarded rate to produce a therapeutic response over a required period of time, optionally including provision for an initial amount of drug being made available within a predetermined time following administration to cause an initial desired therapeutic response); compositions which provide for a "delayed" release of drug (in which the release of drug is delayed until a specific region of the gastrointestinal tract is reached, following which drug release may be either pulsatile or further modified as indicated above); as well as so-called "repeat action" compositions (in which one dose of drug is released either immediately or some time after administration and further doses are released at a later time).

We prefer that the compositions of the invention provide for a delayed release or, more preferably, a sustained (that is prolonged or extended) release of drug over a period of time. More preferred compositions of the invention may be adapted (for example as described herein) to provide a sufficient dose of drug over the dosing interval (irrespective of the number of doses per unit time) to produce a desired therapeutic effect. Release may be uniform and/or constant over an extended period of time, or otherwise.

Compositions of the invention may, for example, be in the form of the following, all of which are well known to those skilled in the art:

(a) Coated pellets, tablets or capsules, which may be designed to release at least some of the drug when the formulation in question reaches a particular region of the gastrointestinal tract. Such tablets may, for example be provided with some form of gastro-resistant coating, such as an enteric coating layer, providing for release of at least part of the drug present in the formulation in a specific part of the gastrointestinal tract, such as the intestinal regions.

(b) Multiple unit or multiparticulate systems, which may be in the form of microparticles, microspheres or pellets comprising drug (which multiple units/multiparticulates may provide for gradual emptying of the formulation containing drug from the stomach into the duodenum and further through the small and large intestine while releasing drug at a pre-determined rate).

(c) Formulations comprising dispersions or solid solutions of active compound in a matrix, which may be in the form of a wax, gum or fat, or, particularly, in the form of a polymer, in which drug release takes place by way of gradual surface erosion of the tablet and/or diffusion.

(d) Systems which comprise a bioadhesive layer, which layer may provide for prolonged retention of composition of the invention in a particular region of the gastrointestinal tract (for example the stomach). This includes floating or sinking systems (that is low and high density systems, respectively), as well as so-called "volume-enlarging" systems.

(e) So-called "pendent" devices, in which drug is attached to an ion exchange resin, which provides for gradual release of drug by way of influence of other ions present in the gastrointestinal tract, for example, the acid environment of the stomach.

(f) Devices in which release rate of drug is controlled by way of its chemical potential (for example the Osmotic Pump).

(g) Systems in which drug is released by diffusion through membranes, including multilayer systems.

(h) Devices that act in accordance with an external signal, to release a small amount of drug.

(i) Active, self-programmed systems, which may contain a sensing element, which element responds to a particular biological environment to modulate drug delivery.

(j) Silastic controlled release depots, which release drug as a function of diffusion of water and/or gastrointestinal fluids into the device via an entry/exit port, resulting in dissolution and subsequent release of drug.

The above principles are discussed at length in prior art references including *Pharmaceutisch Weekblad Scientific Edition*, 6, 57 (1984); *Medical Applications of Controlled Release*, Vol II, eds. Langer and Wise (1984) Boca Raton, Fla., at pages 1 to 34; *Industrial Aspects of Pharmaceuticals*, ed. Sandel, Swedish Pharmaceutical Press (1993) at pages 93 to 104; and pages 191 to 211 of "*Pharmaceutics: The Science of Dosage Form Design*", ed. M. E. Aulton (1988) (Churchill Livingstone); as well as the references cited in the above-mentioned documents, the disclosures in all of which documents are hereby incorporated by reference.

In another aspect the present invention provides an oral modified release formulation wherein $R^2$ is hydroxy or methoxy, (such as Compound A, B, C, G, H or J; $R^2$ is especially methoxy, for example Compound A, B or C) or a pharmaceutically acceptable salt thereof (especially a crystalline salt thereof; such as a $C_{1-6}$ (for example $C_{2-6}$, such as $C_{2-4}$) alkanesulfonic acid salt, or an optionally substituted arylsulfonic acid salt).

The invention includes parenteral modified release formulations using compounds of formula (I). In a further aspect the present invention provides a parenteral modified release formulation wherein $R^2$ is hydrogen (such as Compound D, E or F).

In a still further aspect the invention provides a modified release formulation which comprises a gelling matrix. The matrix preferably comprises hydroxy propyl methyl cellulose (HPMC), iota-carrageenan, sodium dodecyl sulphate (SDS) and/or xanthan gum. More preferably the matrix comprises hydroxy propyl methyl cellulose (HPMC), iota-carrageenan and/or PEO. The HPMC may be one or a mixture of two or more HPMCs of different viscosities or molecular weights (as described anywhere below).

The invention also provides a modified release formulation comprising one or more HPMCs and one or more further components selected from the group comprising: iota-carrageenan, microcrystalline cellulose, a lubricant (such as sodium stearyl fumarate) or mannitol.

The invention further provides, in a further aspect, a modified release formulation comprising xanthan gum; or comprising iota-carrageenan and PEO (as described below).

Suitable modified release formulations may thus be prepared in accordance with standard techniques in pharmacy, as described herein or in the above-mentioned documents, and/ or which are well known.

We prefer that, in the compositions of the invention, active ingredient is provided together with a pharmaceutically acceptable carrier. In particular, we prefer that compositions of the invention are presented in the form of active ingredient in a polymer matrix.

In this respect, we prefer that the compositions of the invention are provided for oral administration in the form of a so-called "swelling" modified-release system, or a "gelling matrix" modified-release system, in which active ingredient is provided together with a polymer that swells in an aqueous medium (that is a "hydrophilic gelling component"). The term "aqueous medium" is to be understood in this context to include water, and liquids which are, or which approximate to, those present in the gastrointestinal tract of a mammal. Such polymer systems typically comprise hydrophilic macromolecular structures, which in a dry form may be in a glassy, or at least partially crystalline, state, and which swell when contacted with aqueous media. Modified release of drug is thus effected by one or more of the following processes: transport of solvent into the polymer matrix, swelling of the polymer, diffusion of drug through the swollen polymer and/or erosion of the polymer, one or more of which may serve to release drug slowly from the polymer matrix into an aqueous medium.

Thus, suitable polymeric materials (acting as carriers), which may be used as the hydrophilic gelling component of a gelling matrix modified-release composition include those with a molecular weight of above 5000 g/mol, and which either:
(a) are at least sparingly soluble in; or
(b) swell when placed in contact with, aqueous media (as defined hereinbefore), so enabling release of drug from the carrier.

Suitable gelling matrix polymers, which may be synthetic or natural, thus include polysaccharides, such as maltodextrin, xanthan, scleroglucan dextran, starch, alginates, pullulan, hyaloronic acid, chitin, chitosan and the like; other natural polymers, such as proteins (albumin, gelatin etc.), poly-L-lysine; sodium poly(acrylic acid); poly (hydroxyalkylmethacrylates) (for example poly (hydroxyethylmethacrylate)); carboxypolymethylene (for example Carbopol™); carbomer; polyvinylpyrrolidone; gums, such as guar gum, gum arabic, gum karaya, gum ghatti, locust bean gum, tamarind gum, gellan gum, gum tragacanth, agar, pectin, gluten and the like; poly(vinyl alcohol); ethylene vinyl alcohol; poly(ethylene oxide) (PEO); and cellulose ethers, such as hydroxymethylcellulose (HMC), hydroxyethylcellulose (HEC), hydroxypropylcellulose (HPC), methylcellulose (MC), ethylcellulose (EC), carboxyethylcellulose (CEC), ethyl hydroxyethylcellulose (EHEC), carboxymethyl hydroxyethylcellulose (CMHEC), hydroxypropylmethylcellulose (HPMC), hydroxypropylethylcellulose (HPEC) and sodium carboxymethylcellulose (Na CMC); as well as copolymers and/or (simple) mixtures of any of the above polymers. Certain of the above-mentioned polymers may further be crosslinked by way of standard techniques.

For the compositions of the invention in the form of gelling matrix systems, we prefer that the principal swelling polymer that is employed is HPC, maltodextrin, scleroglucan or carboxypolymethylene, more preferably, PEO or xanthan, and, especially, HPMC, as well as copolymers and/or (simple) mixtures of any of these polymers. Iota-carrageenan is also preferred.

When PEO, xanthan and HPMC are employed in (that is, as at least one of the polymers of) the hydrophilic gelling component, preferred molecular weights (that is, weight average molecular weights, as determined by standard techniques, such as osmometry, size-exclusion chromatography with a refraction detector (in which molecular weight is determined by way of standard calibration curves), light scattering and/or ultracentrifuge techniques), for these polymers are in the range 5,000 g/mol up to 200,000,000 g/mol, such as up to 100,000,000 g/mol, preferably up to 25,000,000 g/mol and more preferably up to 20,000,000 g/mol. Mixtures of PEO, xanthan and HPMC polymers with different molecular weights within these ranges may be employed.

Suitable HPMC polymers also include those that produce 2% w/w solutions of polymer in water with viscosities, as measured by standard techniques, such as those described generally in the *United States Pharmacopeia* XXIV (USP XXIV/NF19) at page 2002 et seq, as well as, specifically, at pages 843 and 844 (the relevant disclosures in which document are hereby incorporated by reference), of between 3 and 150,000 cps (at 20° C.), such as between 10 and 120,000 cps, preferably between 30 and 50,000 cps and more preferably between 50 and 15,000 cps. Mixtures of HPMC polymers with different viscosities within these ranges may be employed, in order, for example, to produce HPMC mixtures which produce solutions as mentioned above with "average" viscosities (i.e. a viscosity for the mixture) within the above-mentioned preferred ranges. Similarly, mixtures of HPMC polymers (with viscosities and/or "average" viscosities within these ranges) with other above-mentioned polymers may be employed. Suitable HPMC polymers include those fulfilling the *United States Pharmacopeia* standard substitution types 2208, 2906, 2910 and 1828 (see USP XXIV/NF19 for further details). Suitable HPMC polymers thus include those sold under the trademark METHOCEL™ (Dow Chemical Corporation) or the trademark METOLOSE™ (Shin-Etsu).

Suitable xanthan polymers include those that produce 1% w/w solutions of polymer in water with viscosities, as measured by standard techniques, such as those described generally in the *United States Pharmacopeia* XXIV (USP XXIV/NF19) at page 2002 et seq, as well as, specifically, at pages 2537 and 2538 (the relevant disclosures in which document are hereby incorporated by reference), of between 60 and 2,000 cps (at 24° C.), for example between 600 and 1,800 cps and preferably between 1,200 and 1,600 cps. Mixtures of xanthan polymers with different viscosities within these ranges may be employed, in order, for example, to produce xanthan mixtures which produce solutions as mentioned above with "average" viscosities (i.e. a viscosity for the mixture) within the above-mentioned preferred ranges. Similarly, mixtures of xanthan polymers (with viscosities and/or "average" viscosities within these ranges) with other above-mentioned polymers may be employed. Suitable xanthan polymers include those sold under the trademarks XANTURAL™ and KELTROL™ (CPKelco), and SATIAXANE™ (Degussa, Texturant Systems).

The choice of polymer will be determined by the nature of the active ingredient/drug that is employed in the composition of the invention as well as the desired rate of release. In particular, it will be appreciated by the skilled person, for example in the case of HPMC, that a higher molecular weight will, in general, provide a slower rate of release of drug from the composition. Furthermore, in the case of HPMC, different degrees of substitution of methoxyl groups and hydroxypropoxyl groups will give rise to changes in the rate of release of drug from the composition. In this respect, and as stated above, it may be desirable to provide compositions of the invention in the form of gelling matrix systems in which the polymer carrier is provided by way of a blend of two or more polymers of, for example, different molecular weights, for example as described hereinafter, in order to produce a particular required or desired release profile.

When in the form of gelling matrix systems, we have also found that rate of release of drug from compositions of the invention may be further controlled by way of controlling the drug:polymer ratio within, and the surface area:volume ratio of, individual compositions (for example tablets) comprising drug and polymer carrier system.

Compositions of the invention, whether in the form of a gelling matrix system or otherwise, may contain one or more further excipients (in addition to the polymer carrier system) to further modify drug release, to improve the physical and/or chemical properties of the final composition, and/or to facilitate the process of manufacture. Such excipients are conventional in the formulation of modified release compositions.

For example, compositions of the invention may contain one or more of the following diluents: calcium phosphate (monocalcium phosphate, dicalcium phosphate and tricalcium phosphate), lactose, microcrystalline cellulose, mannitol, sorbitol, titanium dioxide, aluminium silicate and the like. Preferred diluents include microcrystalline cellulose and also mannitol.

Compositions of the invention may contain one or more of the following lubricants: magnesium stearate, sodium stearyl fumarate and the like.

Compositions of the invention may contain a glidant, such as a colloidal silica.

Compositions of the invention may contain one or more of the following binders: polyvinylpyrrolidone, lactose, mannitol, microcrystalline cellulose, a polyethylene glycol (PEG), a HPMC of a low molecular weight, a MC of a low molecular weight, a HPC of a low molecular weight and the like. Preferred binders include microcrystalline cellulose.

Compositions of the invention may contain one or more of the following pH controlling agents: organic acids (for example citric acid and the like) or alkali metal (for example sodium) salts thereof, pharmaceutically acceptable salts (for example sodium, magnesium or calcium salts) of inorganic acids (such as carbonic acid or phosphoric acid), oxides of magnesium, as well as alkali, and alkaline earth metal (for example sodium, calcium, potassium and the like) sulphates, metabisulphates, propionates and sorbates.

Other further excipients may include colourants, flavourings, solubilising agents (such as SDS), coating agents, preservatives, etc.

Combinations of the above-stated further excipients may be employed.

It will be appreciated that some of the above mentioned further excipients, which may be present in the final composition of the invention, may have more than one of the above-stated functions. Moreover, further excipients mentioned above may also function as part of a hydrophilic gelling component in a gelling matrix system.

The total amount of further excipients (not including, in the case of gelling matrix systems, the principal polymer carrier(s)) that may be present in the composition of the invention will depend upon the nature of the composition, as well as the nature, and amounts of, the other constituents of that composition, and may be an amount of up to 85%, for example between 0.1 to 75%, such as 0.2 to 65%, preferably 0.3 to 55%, more preferably 0.5 to 45% and especially 1 to 40%, such as 2 to 35% w/w. In any event, the choice, and amount, of excipient(s) may be determined routinely (that is without recourse to inventive input) by the skilled person.

In gelling matrix systems, the amount of polymer in the system should be enough to ensure that a sufficient dose of drug is provided over the dosing interval to produce the desired therapeutic effect. Thus, for a gelling matrix system, we prefer that it takes at least 2 hours (preferably at least 4 hours, especially at least 6 hours) for 80% (especially 60%) of the initial drug content of the composition to be released to a patient after administration under the test conditions described hereinafter, and particularly over a period of between 8 and 24 hours. Most preferably at least 80% of the initial drug content of the composition is released at a time somewhere between 8 and 24 hours. Suitable amounts of polymer that may be included, which will depend upon inter alia the active ingredient that is employed to in the composition, any excipients that may be present and the nature of the polymer that is employed, are in the range 5 to 99.5%, for example 10 to 95%, preferably 30 to 80% w/w. In any event, the choice, and amount, of polymer may be determined routinely by the skilled person.

In another preferred formulation we prefer that the compounds of the invention are formulated together in a gelling matrix composition comprising iota-carrageenan and one or more neutral gelling polymers.

Iota-carrageenan is preferably present in such a preferred preparation at a level of more that 15% by weight. Preferred grades of iota-carrageenan include pharmaceutical grade iota-carrageenan (for example, available from FMC Biopolymer), which has a viscosity of not less than 5 centipoise (cps), preferably in the range 5-10 cps (for a 1.5% solution warmed to 82° C., after which the viscosity is measured at 75° C. with a Brookfield LV viscometer fitted with a #1 spindle running at a speed of 30 rpm), and technical grade iota-carrageenan (for example, available from Fluka Biochemica), which preferably has a viscosity of not less than 14 mPa·s, for a 0.3% aqueous solution warmed to 20° C., after which the viscosity is measured using a fallingball viscometer, of type Haake, used together with a Lauda thermostat C3 and Hakke Mess-System III, and using gold-coated stainless steel balls of density 7.8 g/cm$^3$.

The neutral gelling polymer may be a single, or a mixture of more than one, neutral polymer(s) having gelling properties and having substantially pH-independent solubility. The neutral gelling polymer is, preferably, present in the formulation at a level of more that 10% but preferably more than 20% by weight.

Suitable neutral gelling polymers include polyethylene oxide (PEO), derivatives and members of the PEO family (for example, polyethylene glycol (PEG)), preferably existing naturally in the solid state, of suitable molecular weight or viscosity. If used as a single neutral gelling polymer, a PEO preferably has a MW of $\geq$4 million (4M), corresponding to an aqueous solution viscosity range of 1650-5500 mPa·s (or 1650-5500 cps; measured for a 1% aqueous solution at 25° C., using a Brookfield RVF viscometer, with No. 2 spindle, at 2 rpm). Other examples of suitable PEOs include a PEO of MW around 5 million (5M), corresponding to an aqueous solution viscosity range of 5500-7500 mPa·s, or a PEO MW around 8 million (8M), corresponding to an aqueous solution viscosity range of 10000-15000 mPa·s. This range covers the value for typical solution viscosity (in cps) measured at 25° C., quoted for this polymer, in the USP 24/NF 19, 2000 edition, pp. 2285-2286. If PEG is used as a single neutral gelling polymer it preferably has a high molecular weight, for example, a MW of around 20000, corresponding to a viscosity range of 2700-3500 mPa·s (or 2700-3500 cps), measured using a 50% aqueous solution (w/w) at 20° C., using a capillary viscometer (Ubbelohde or equivalent). [Ref: European Pharmacopoeia 3$^{rd}$ Ed., 2000, Supplement, pp. 908-909.]

Other suitable neutral gelling polymers include cellulose derivatives such as hydroxypropylmethyl cellulose (HPMC) or hydroxyethylcellulose (HEC) with suitably high viscosities (for example "HPMC 50 cps", "HPMC 10000 cps", "HPMC 15000 cps", "HEC type HH" or "HEC type H"). When used as a single neutral polymer, hydroxypropylmethyl cellulose polymers like "HPMC 10000 cps" and "HPMC 15000 cps" have, respectively, apparent viscosities of 7500-14000 mPa·s (or 7500-14000 cps), and 11250-21000 mPa·s (or 11250-21000 cps), when measured at 20° C. with a 2% (w/w) aqueous solution, calculated with reference to the dried substance, using a capillary viscometer (Ubbelohde or equivalent). One type of hydroxyethylcellulose polymer, for example, "Natrosol 250 Pharma, type HH", from Hercules Incorporated (Aqualon), shows typically a Brookfield viscosity of about 20,000 mPa·s using a Brookfield Synchro-Lectric Model LVF instrument, at the conditions 1% solution concentration, spindle no. 4, spindle speed 30 rpm, factor 200, 25° C. (See Natrosol Physical and Chemical Properties booklet, 33.007-E6 (1993), p. 21).

Particular formulations that may be mentioned include those in which compound of the invention is formulated together with iota-carageenan and HPMC (10,000 cps) in a 50:50 (wt %) ratio, or together with iota-carageenan and HPMC (50 cps) & HPMC (10,000 cps) in a 35:60:5 (wt %) ratio, or together with iota-carageenan and PEO 4M in a 50:50 (wt %) ratio, Preferred additional excipients in such formulations include lubricants, such as sodium stearyl fumarate.

In one aspect the invention provides a non-injectable formulation of the invention to comprising Compound A, B or C or a salt thereof; an HPMC and a lubricant (such as sodium stearyl fumarate). In a further aspect the formulation may comprise a mixture of 2 or more HPMCs of different viscosities (such as 10,000 cPs and 50 cPs). Further, the formulation may additionally comprise a solubilising agent [such as sodium dodecyl sulphate (SDS), sodium lauryl sulphate or polyoxyl 40 hydrogenated castor oil].

Suitable amounts of active ingredient in the compositions of the invention, whether in the form of gelling matrix systems or otherwise, depend upon many factors, such as the nature of that ingredient (free base/salt etc), the dose that is required, and the nature, and amounts, of other constituents of the composition. However, they may be in the range 0.5 to 80%, for example 1 to 75%, such as 3 to 70%, preferably 5 to 65%, more preferably 10 to 60% and especially 15 to 55% w/w. In any event, the amount of active ingredient to be included may be determined routinely by the skilled person.

A typical daily dose of a compound of formula (I), or a pharmaceutically acceptable salt thereof, is in the range 0.001 to 100 mg/kg body weight of free base (that is, in the case of a salt, excluding any weight resulting from the presence of a counter ion), irrespective of the number of individual doses that are administered during the course of that day. A preferred daily dose is in the range 20-500 mg.

Compositions of the invention such as those described hereinbefore may be made in accordance with well known techniques such as those described in the references mentioned hereinbefore. Compositions of the invention that are in the form of gelling matrix systems may be prepared by standard techniques, and using standard equipment, known to the skilled person, including wet or dry granulation, direct compression/compaction, drying, milling, mixing, tabletting and coating, as well as combinations of these processes, for example as described hereinafter.

Although compositions of the invention are preferably adapted to be administered orally, their use is not limited to that mode of administration. Parenteral modified release compositions of the invention, which may include systems that are well known to those skilled in the art, such as those based upon poloxamers, biodegradable microspheres, liposomes, suspensions in oils and/or emulsions, may be prepared in accordance with standard techniques, for example as described by Leung et al in "*Controlled Drug Delivery: Fundamentals and Applications*" (*Drugs and the Pharmaceutical Sciences*; vol. 29), $2^{nd}$ edition, eds. Robinson and Lee, Dekker (1987) at Chapter 10, page 433, the disclosure in which document is hereby incorporated by reference.

The compositions of the invention may be dosed once or more times daily (preferably once, but no more than twice, daily), irrespective of the number of individual units (formulations/compositions) that are administered as part of one "dose".

The formulations of the invention are administered to mammalian patients (including humans), and, for compounds of formula (I) wherein $R^2$ is not hydrogen, are thereafter metabolised in the body to form compounds of formula (I) wherein $R^2$ is hydrogen that are pharmacologically active.

According to a further aspect of the invention there is thus provided a formulation of the invention for use as a pharmaceutical.

In particular, the compounds of formula (I) are, or are metabolised following administration to form, potent inhibitors of thrombin, for example as may be demonstrated in the tests described in inter alia international patent application No. PCT/SE01/02657, as well as international patent applications WO 02/14270, WO 01/87879 and WO 00/42059, the relevant disclosures in which documents are hereby incorporated by reference.

By "prodrug of a thrombin inhibitor", we include compounds that are metabolised following administration and form a thrombin inhibitor, in an experimentally-detectable amount, following administration.

By "active ingredient" and "active substance" we mean the pharmaceutical agent (covering thrombin inhibitor and prodrugs thereof) present in the formulation.

The formulations of the invention are thus expected to be useful in those conditions where inhibition of thrombin is required, and/or conditions where anticoagulant therapy is indicated, including the following:

The treatment and/or prophylaxis of thrombosis and hypercoagubility in blood and/or tissues of animals including man. It is known that hypercoagubility may lead to thrombo-embolic diseases. Conditions associated with hypercoaguability and thrombo-embolic diseases which may be mentioned include inherited or acquired activated protein C resistance, such as the factor V-mutation (factor V Leiden), and inherited or acquired deficiencies in antithrombin III, protein C, protein S, heparin cofactor II. Other conditions known to be associated with hypercoaguability and thrombo-embolic disease include circulating antiphospholipid antibodies (Lupus anticoagulant), homocysteinemi, heparin induced thrombocytopenia and defects in fibrinolysis, as well as coagulation syndromes (for example disseminated intravascular coagulation (DIC)) and vascular injury in general (for example due to surgery).

The treatment of conditions where there is an undesirable excess of thrombin without signs of hypercoaguability, for example in neurodegenerative diseases such as Alzheimer's disease.

Particular disease states which may be mentioned include the therapeutic and/or prophylactic treatment of venous thrombosis (for example DVT) and pulmonary embolism, arterial thrombosis (e.g. in myocardial infarction, unstable angina, thrombosis-based stroke and peripheral arterial thrombosis), and systemic embolism usually from the atrium during atrial fibrillation (for example non-valvular atrial fibrillation) or from the left ventricle after transmural myocardial infarction, or caused by congestive heart failure; prophylaxis of re-occlusion (that is thrombosis) after thrombolysis, percutaneous trans-luminal angioplasty (PTA) and coronary bypass operations; the prevention of re-thrombosis after microsurgery and vascular surgery in general.

Further indications include the therapeutic and/or prophylactic treatment of disseminated intravascular coagulation caused by bacteria, multiple trauma, intoxication or any other mechanism; anticoagulant treatment when blood is in contact with foreign surfaces in the body such as vascular grafts, vascular stents, vascular catheters, mechanical and biological prosthetic valves or any other medical device; and anticoagulant treatment when blood is in contact with medical devices outside the body such as during cardiovascular surgery using a heart-lung machine or in haemodialysis; the therapeutic and/or prophylactic treatment of idiopathic and adult respiratory distress syndrome, pulmonary fibrosis following treatment with radiation or chemotherapy, septic shock, septicemia, inflammatory responses, which include, but are not limited to, edema, acute or chronic atherosclerosis such as coronary arterial disease and the formation of atherosclerotic plaques, cerebral arterial disease, cerebral infarction, cerebral thrombosis, cerebral embolism, peripheral arterial disease, ischaemia, angina (including unstable angina), reperfusion damage, restenosis after percutaneous trans-luminal angioplasty (PTA) and coronary artery bypass surgery.

The formulation of the present invention may also comprise any antithrombotic agent(s) with a different mechanism of action to that of the compounds of formula (I), such as one or more of the following: the antiplatelet agents acetylsalicylic acid, ticlopidine and clopidogrel; thromboxane receptor and/or synthetase inhibitors; fibrinogen receptor antagonists; prostacyclin mimetics; phosphodiesterase inhibitors; ADP-receptor ($P_2T$) antagonists; and inhibitors of carboxypeptidase U (CPU).

Compounds of formula (I) that inhibit trypsin and/or thrombin may also be useful in the treatment of pancreatitis.

The formulations of the invention are thus indicated both in the therapeutic and/or prophylactic treatment of these conditions.

The formulations of the invention are useful in the delivery of a compound of formula (I) or a salt thereof to a patient. As the compounds of formula (I), and salts thereof, are useful in both the prophylaxis and the treatment of thrombosis, the formulations of the invention are also useful in the treatment of such a disorder.

According to a further aspect of the invention, there is provided a method of treatment of thrombosis which method comprises administration of a formulation of the invention to a person suffering from, or susceptible to, such a condition.

In a still further aspect the present invention provides a formulation of the invention in the manufacture of a medicament for use in the treatment of thrombosis.

For the avoidance of doubt, by "treatment" we include the therapeutic treatment, as well as the prophylaxis, of a condition.

The compositions of the invention have the advantage that they may provide a modified release of the compounds of formula (I) or a pharmaceutically acceptable salt of any of these compounds, in order to obtain a more even and/or prolonged effect against thrombosis and may thus provide efficient dosing of active ingredient preferably no more than once or twice daily.

Compositions of the invention may also have the advantage that they may be prepared using established pharmaceutical processing methods and employ materials that are approved for use in foods or pharmaceuticals or of like regulatory status.

Compounds of formula (I) can be prepared using the following procedures.

General Procedures

TLC was performed on silica gel. Chiral HPLC analysis was performed using a 46 mm×250 mm Chiralcel OD column with a 5 cm guard column. The column temperature was maintained at 35° C. A flow rate of 1.0 mL/min was used. A Gilson 115 UV detector at 228 nm was used. The mobile phase consisted of hexanes, ethanol and trifluoroacetic acid and the appropriate ratios are listed for each compound. Typically, the product was dissolved in a minimal amount of ethanol and this was diluted with the mobile phase.

In Preparations A to I below, LC-MS/MS was performed using a HP-1100 instrument equipped with a CTC-PAL injector and a 5 Tm, 4×100 mm ThermoQuest, Hypersil BDS-C18 column. An API-3000 (Sciex) MS detector was used. The flow rate was 1.2 mL/min and the mobile phase (gradient) consisted of 10-90% acetonitrile with 90-10% of 4 mM aq. ammonium acetate, both containing 0.2% formic acid. Otherwise, low resolution mass spectra (LRMS) were recorded using a Micromass ZQ spectrometer in ESI posneg switching ion mode (mass range m/z 100-800); and high resolution mass spectra (HRMS) were recorded using a Micromass LCT spectrometer in ES negative ionization mode (mass range m/z 100-1000) with Leucine Enkephalin ($C_{28}H_{37}N_5O_7$) as internal mass standard.

[1] H NMR spectra were recorded using tetramethylsilane as the internal standard.

Processes for the synthesis of compounds of formula (I) are contained in International Patent Application No. PCT/SE01/02657 (WO 02/44145, earliest priority date 1 Dec. 2000, filed 30 Nov. 2001, published 6 Jun. 2002)), relevant information from which is incorporated herein.

Preparation A: Preparation of Compound A (i) 3-Chloro-5-methoxybenzaldehyde 3,5-Dichloroanisole (74.0 g, 419 mmol) in THF (200 mL) was added dropwise to magnesium metal (14.2 g, 585 mmol, pre-washed with 0.5 N HCl) in THF (100 mL) at 25° C. After the addition, 1,2-dibromoethane (3.9 g, 20.8 mmol) was added dropwise. The resultant dark brown mixture was heated at reflux for 3 h. The mixture was cooled to 0° C., and N,N-dimethylformamide (60 mL) was added in one portion. The mixture was partitioned with diethyl ether (3×400 mL) and 6N HCl (500 mL). The combined organic extracts were washed with brine (300 mL), dried ($Na_2SO_4$), filtered and concentrated in vacuo to give an oil. Flash chromatography (2×) on silica gel eluting with Hex:EtOAc (4:1) afforded the sub-title compound (38.9 g, 54%) as a yellow oil.

$^1$H NMR (300 MHz, $CDCl_3$) δ 9.90 (s, 1H), 7.53 (s, 1H), 7.38 (s, 1H), 7.15 (s, 1H), 3.87 (s, 3H).

(ii) 3-Chloro-5-hydroxybenzaldehyde

A solution of 3-chloro-5-methoxybenzaldehyde (22.8 g, 134 mmol; see step (i) above) in $CH_2Cl_2$ (250 mL) was cooled to 0° C. Boron tribromide (15.8 mL, 167 mmol) was added dropwise over 15 min. After stirring, the reaction mixture for 2 h, $H_2O$ (50 mL) was added slowly. The solution was then extracted with $Et_2O$ (2×100 mL). The organic layers were combined, dried ($Na_2SO_4$), filtered and concentrated in vacuo. Flash chromatography on silica gel eluting with Hex:EtOAc (4:1) afforded the sub-title compound (5.2 g, 25%).

$^1$H NMR (300 MHz, $CDCl_3$) δ 9.85 (s, 1H), 7.35 (s, 1H), 7.20 (s,1H), 7.10 (s,1H), 3.68 (s,1H)

(iii) 3-Chloro-5-difluoromethoxybenzaldehyde

A solution of 3-chloro-5-hydroxybenzaldehyde (7.5 g, 48 mmol; see step (ii) above) in 2-propanol (250 mL) and 30% KOH (100 mL) was heated to reflux. While stirring, $CHClF_2$ was bubbled into the reaction mixture for 2 h. The reaction mixture was cooled, acidified with 1N HCl and extracted with EtOAc (2×100 mL). The organics were washed with brine (100 mL), dried ($Na_2SO_4$), filtered and concentrated in vacuo. Flash chromatography on silica gel eluting with Hex:EtOAc (4:1) afforded the sub-title compound (4.6 g, 46%).

$^1$H NMR (300 MHz, $CDCl_3$) δ 9.95 (s, 1H), 7.72 (s, 1H), 7.52 (s, 1H), 7.40 (s, 1H), 6.60 (t, $J_{H-F}$=71.1 Hz, 1H)

(iv) Ph(3-Cl)(5-OCHF$_2$)—(R,S)CH(OTMS)CN

A solution of 3-chloro-5-difluoromethoxybenzaldehyde (4.6 g, 22.3 mmol; see step (iii) above) in $CH_2Cl_2$ (200 mL) was cooled to 0° C. $ZnI_2$ (1.8 g, 5.6 mmol) and trimethylsilyl cyanide (2.8 g, 27.9 mmol) were added and the reaction mixture was allowed to warm to room temperature and stirred for 15 h. The mixture was partially concentrated in vacuo yielding the sub-title compound as a liquid, which was used directly in step (v) below without further purification or characterization.

(v) Ph(3-Cl)(5-OCHF$_2$)—(R,S)CH(OH)C(NH)OEt

Ph(3-Cl)(5-OCHF$_2$)—(R,S)CH(OTMS)CN (6.82 g, assume 22.3 mmol; see step (iv) above) was added dropwise to HCl/EtOH (500 mL). The reaction mixture was stirred 15 h, then partially concentrated in vacuo yielding the sub-title compound as a liquid, which was used in step (vi) without further purification or characterization.

(vi) Ph(3-Cl)(5-OCHF$_2$)—(R,S)CH(OH)C(O)OEt

Ph(3-Cl)(5-OCHF$_2$)—(R,S)CH(OH)C(NH)OEt (6.24 g, assume 22.3 mmol; see step (v) above) was dissolved in THF (250 mL), 0.5M H$_2$SO$_4$ (400 mL) was added and the reaction was stirred at 40° C. for 65 h, cooled and then partially concentrated in vacuo to remove most of the THF. The reaction mixture was then extracted with Et$_2$O (3×100 mL), dried (Na$_2$SO$_4$), filtered and concentrated in vacuo to afford the sub-title compound as a solid, which was used in step (vii) without further purification or characterization.

(vii) Ph(3-Cl)(5-OCHF$_2$)—(R,S)CH(OH)C(O)OH

A solution of Ph(3-Cl)(5-OCHF$_2$)—(R,S)CH(OH)C(O)OEt (6.25 g, assume 22.3 mmol; see step (vi) above) in 2-propanol (175 mL) and 20% KOH (350 mL) was stirred at room temperature 15 h. The reaction was then partially concentrated in vacuo to remove most of the 2-propanol. The remaining mixture was acidified with 1M H$_2$SO$_4$, extracted with Et$_2$O (3×100 mL), dried (Na$_2$SO$_4$) and concentrated in vacuo to give a solid. Flash chromatography on silica gel eluting with CHCl$_3$:MeOH:concentrated NH$_4$OH (6:3:1) afforded the ammonium salt of the sub-title compound. The ammonium salt was then dissolved in a mixture of EtOAc (75 mL) and H$_2$O (75 mL) and acidified with 2N HCl. The organic layer was separated and washed with brine (50 mL), dried (Na$_2$SO$_4$) and concentrated in vacuo to afford the sub-title compound (3.2 g, 57% from steps (iv) to (vii)).

$^1$H NMR (300 MHz, CD$_3$OD) δ 7.38 (s, 1H), 7.22 (s, 1H), 7.15 (s, 1H), 6.89 (t, J$_{H-F}$=71.1 Hz, 1H), 5.16 (s, 1H)

(viii) Ph(3-Cl)(5-OCHF$_2$)—(R)CH(OH)C(O)OH (a) and Ph(3-Cl)(5-OCHF$_2$)—(S)CH(OAc)C(O)OH (b)

A mixture of Ph(3-Cl)(5-OCHF$_2$)—(R,S)CH(OH)C(O)OH (3.2 g, 12.7 mmol; see step (vii) above) and Lipase PS "Amano" (~2.0 g) in vinyl acetate (125 mL) and MTBE (125 mL) was heated at reflux for 48 h. The reaction mixture was cooled, filtered through Celite® and the filter cake washed with EtOAc. The filtrate was concentrated in vacuo and subjected to flash chromatography on silica gel eluting with CHCl$_3$:MeOH:concentrated NH$_4$OH (6:3:1) yielding the ammonium salts of the sub-title compounds (a) and (b). Compound (a) as a salt was dissolved in H$_2$O, acidified with 2N HCl and extracted with EtOAc. The organic layer was washed with brine, dried (Na$_2$SO$_4$), filtered and concentrated in vacuo to afford the sub-title compound (a) (1.2 g, 37%).

For sub-title compound (a)
$^1$H NMR (300 MHz, CD$_3$OD) δ 7.38 (s, 1H), 7.22 (s, 1H), 7.15 (s, 1H), 6.89 (t, J$_{H-F}$=71.1 Hz, 1H), 5.17 (s, 1H)

(ix) Ph(3-Cl)(5-OCHF$_2$)—(R)CH(OH)C(O)-Aze-Pab(Teoc)

To a solution of Ph(3-Cl)(5-OCHF$_2$)—(R)CH(OH)C(O)OH (1.1 g, 4.4 mmol; see step (viii) above) and H-Aze-Pab (Teoc) (see international patent application WO 00/42059, 2.6 g, 5.7 mmol) in DMF (50 mL) at 0° C. was added PyBOP (2.8 g, 5.3 mmol) and collidine (1.3 g, 10.6 mmol). The reaction was stirred at 0° C. for 2 h and then at room temperature for an additional 15 h. The reaction mixture was concentrated in vacuo and flash chromatographed on silica gel (3×), eluting first with CHCl$_3$:EtOH (9:1), then with EtOAc:EtOH (20:1) and finally eluting with CH$_2$Cl$_2$:CH$_3$OH (95:5) to afford the sub-title compound (1.0 g, 37%) as a white solid.

$^1$H NMR (300 MHz, CD$_3$OD, mixture of rotamers) δ 7.79-7.85 (d, J=8.7 Hz, 2H), 7.15-7.48 (m, 5H), 6.89 and 6.91 (t, J$_{H-F}$=71.1 Hz, 1H), 5.12 and 5.20 (s, 1H), 4.75-4.85 (m, 1H), 3.97-4.55 (m, 6H), 2.10-2.75 (m, 2H), 1.05-1.15 (m, 2H), 0.09 (s, 9H)

MS (m/z) 611 (M+1)$^+$ (x) Ph(3-Cl)(5-OCHF$_2$)—(R)CH(OH)C(O)-Aze-Pab (OMe, Teoc)

Ph(3-Cl)(5-OCHF$_2$)—(R)CH(OH)C(O)-Aze-Pab(Teoc) (0.40 g, 0.65 mmol; see step (ix) above), was dissolved in 20 mL of acetonitrile and 0.50 g (6.0 mmol) of O-methyl hydroxylamine hydrochloride was added. The mixture was heated at 70° C. for 2 h. The solvent was evaporated and the residue was partitioned between water and ethyl acetate. The aqueous phase was extracted twice more with ethyl acetate and the combined organic phase was washed with water, brine, dried (Na$_2$SO$_4$), filtered and evaporated. Yield: 0.41 g (91%).

$^1$H-NMR (400 MHz; CDCl$_3$): δ 7.83 (bt, 1H), 7.57 (bs, 1H), 7.47 (d, 2H), 7.30 (d, 2H), 7.20 (m, 1H), 7.14 (m, 1H), 7.01 (m, 1H), 6.53 (t, 1H), 4.89 (s, 1H), 4.87 (m, 1H), 4.47 (m, 2H), 4.4-4.2 (b, 1H), 4.17-4.1 (m, 3H), 3.95 (s, 3H), 3.67 (m, 1H), 2.68 (m, 1H), 2.42 (m, 1H) 0.97 (m, 2H), 0.01 (s, 9H).

(xi) Compound A

Ph(3-Cl)(5-OCHF$_2$)—(R)CH(OH)C(O)-Aze-Pab(OMe, Teoc) (0.40 g, 0.62 mmol; see step (x) above), was dissolved in 5 mL of TFA and allowed to react for 30 min. TFA was evaporated and the residue was partitioned between ethyl acetate and NaHCO$_3$ (aq.). The aqueous phase was extracted twice more with ethyl acetate and the combined organic phase was washed with water, brine, dried (Na$_2$SO$_4$), filtered and evaporated. The product was freeze dried from water/acetonitrile. No purification was necessary. Yield: 0.28 g (85%).

$^1$H-NMR (600 MHz; CDCl$_3$): δ 7.89 (bt, 1H), 7.57 (d, 2H), 7.28 (d, 2H), 7.18 (m, 1H), 7.13 (m, 1H), 6.99 (m, 1H), 6.51 (t, 1H), 4.88 (s, 1H), 4.87 (m, 1H), 4.80 (bs, 2H), 4.48 (dd, 1H), 4.43 (dd, 1H), 4.10 (m, 1H), 3.89 (s, 3H), 3.68 (m, 1H), 2.68 (m, 1H), 2.40 (m, 1H).

$^{13}$C-NMR (125 MHz; CDCl$_3$): (carbonyl and/or amidine carbons, rotamers) δ 172.9, 170.8, 152.7, 152.6

HRMS calculated for C$_{22}$H$_{23}$ClF$_2$N$_4$O$_5$ (M−H)$^-$ 495.1242, found 495.1247.

Preparation B: Preparation of Compound B (i) 2,6-Difluoro-4[(methylsulfinyl)(methylthio)methyl]benzonitrile (Methylsulfinyl)(methylthio)methane (7.26 g, 0.0584 mol) was dissolved in 100 mL of dry THF under argon and was cooled to −78° C. Butyllithium in hexane (16 mL 1.6M, 0.0256 mol) was added dropwise with stirring. The mixture was stirred for 15 min. Meanwhile, a solution of 3,4,5-trifluorobenzonitrile (4.0 g, 0.025 mmol) in 100 mL of dry THF was cooled to −78° C. under argon and the former solution was added through a cannula to the latter solution over a period of 35 min. After 30 min, the cooling bath was removed and when the reaction had reached room temperature it was poured into 400 mL of water. The THF was evaporated and the remaining aqueous layer was extracted three times with diethyl ether. The combined ether phase was washed with water, dried ($Na_2SO_4$) and evaporated. Yield: 2.0 g (30%).

$^1$H NMR (500 MHz, $CDCl_3$) δ 7.4-7.25 (m, 2H), 5.01 (s, 1H, diastereomer), 4.91 (s, 1H, diastereomer), 2.88 (s, 3H, diastereomer), 2.52 (s, 3H, diastereomer), 2.49 (s, 3H, diastereomer), 2.34 (s, 3H, diastereomer), 1.72 (broad, 1H)

(ii) 2,6-Difluoro-4-formylbenzonitrile 2,6-Difluoro-4[(methylsulfinyl)(methylthio)methyl]benzonitrile (2.17 g, 8.32 mmol; see step (i) above) was dissolved in 90 mL of THF and 3.5 mL of concentrated sulfuric acid was added. The mixture was left at room temperature for 3 days and subsequently poured into 450 mL of water. Extraction three times with EtOAc followed and the combined ethereal phase was washed twice with aqueous sodium bicarbonate and with brine, dried ($Na_2SO_4$) and evaporated.

Yield: 1.36 g (98%). The position of the formyl group was established by $^{13}$C NMR. The signal from the fluorinated carbons at 162.7 ppm exhibited the expected coupling pattern with two coupling constants in the order of 260 Hz and 6.3 Hz respectively corresponding to an ipso and a meta coupling from the fluorine atoms.

$^1$H NMR (400 MHz, $CDCl_3$) δ 10.35 (s, 1H), 7.33 (m, 2H)

(iii) 2,6-Difluoro-4-hydroxymethylbenzonitrile 2,6-Difluoro-4-formylbenzonitrile (1.36 g, 8.13 mmol; see step (ii) above) was dissolved in 25 mL of methanol and cooled on an ice bath. Sodium borohydride (0.307 g, 8.12 mmol) was added in portions with stirring and the reaction was left for 65 min. The solvent was evaporated and the residue was partitioned between diethyl ether and aqueous sodium bicarbonate. The ethereal layer was washed with more aqueous sodium bicarbonate and brine, dried ($Na_2SO_4$) and evaporated. The crude product crystallised soon and could be used without further purification.

Yield: 1.24 g (90%).

$^1$H NMR (400 MHz, $CDCl_3$) δ 7.24 (m, 2H), 4.81 (s, 2H), 2.10 (broad, 1H)

(iv) 4-Cyano-2,6-difluorobenzyl methanesulfonate

To an ice cooled solution of 2,6-difluoro-4-hydroxymethylbenzonitrile (1.24 g, 7.32 mmol; see step (iii) above) and methanesulfonyl chloride (0.93 g, 8.1 mmol) in 60 mL of methylene chloride was added triethylamine (0.81 g, 8.1 mmol) with stirring. After 3 h at 0° C., the mixture was washed twice with 1M HCl and once with water, dried ($Na_2SO_4$) and evaporated. The product could be used without further purification. Yield: 1.61 g (89%).

$^1$H NMR (300 MHz, $CDCl_3$) δ 7.29 (m, 2H), 5.33 (s, 2H), 3.07 (s, 3H)

(v) 4-Azidomethyl-2,6-difluorobenzonitrile

A mixture of 4-cyano-2,6-difluorobenzyl methanesulfonate (1.61 g, 6.51 mmol; see step (iv) above) and sodium azide (0.72 g, 0.0111 mol) in 10 mL of water and 20 mL of DMF was stirred at room temperature overnight. The resultant was subsequently poured into 200 mL of water and extracted three times with diethyl ether. The combined ethereal phase was washed five times with water, dried ($Na_2SO_4$) and evaporated. A small sample was evaporated for NMR purposes and the product crystallised. The rest was evaporated cautiously but not until complete dryness. Yield (theoretically 1.26 g) was assumed to be almost quantitative based on NMR and analytical HPLC.

$^1$H NMR (400 MHz, $CDCl_3$) δ 7.29 (m, 2H), 4.46 (s, 2H)

(vi) 4-Aminomethyl-2,6-difluorobenzonitrile

This reaction was carried out according to the procedure described in J. Chem. Res. (M) (1992) 3128. To a suspension of 520 mg of 10% Pd/C (50% moisture) in 20 mL of water was added a solution of sodium borohydride (0.834 g, 0.0221 mol) in 20 mL of water. Some gas evolution resulted. 4-Azidomethyl-2,6-difluorobenzonitrile (1.26 g, 6.49 mmol; see step (v) above) was dissolved in 50 mL of THF and added to the aqueous mixture on an ice bath over 15 min. The mixture was stirred for 4 h, whereafter 20 mL of 2M HCl was added and the mixture was filtered through Celite. The Celite was rinsed with more water and the combined aqueous phase was washed with EtOAc and subsequently made alkaline with 2M NaOH. Extraction three times with methylene chloride followed and the combined organic phase was washed with water, dried ($Na_2SO_4$) and evaporated. Yield: 0.87 g (80%).

$^1$H NMR (400 MHz, $CDCl_3$) δ 7.20 (m, 2H), 3.96 (s, 2H), 1.51 (broad, 2H)

(vii) 2,6-Difluoro-4-tert-butoxycarbonylaminomethylbenzonitrile

A solution of 4-aminomethyl-2,6-difluorobenzonitrile (0.876 g, 5.21 mmol; see step (vi) above) was dissolved in 50 mL of THF and di-tert-butyl dicarbonate (1.14 g, 5.22 mmol) in 10 mL of THF was added. The mixture was stirred for 3.5 h. The THF was evaporated and the residue was partitioned between water and EtOAc. The organic layer was washed three times with 0.5 M HCl and water, dried ($Na_2SO_4$) and evaporated. The product could be used without further purification. Yield: 1.38 g (99%).

$^1$H NMR (300 MHz, $CDCl_3$) δ 7.21 (m, 2H), 4.95 (broad, 1H), 4.43 (broad, 2H), 1.52 (s, 9H)

(viii) Boc-Pab(2,6-diF)(OH)

A mixture of 2,6-difluoro-4-tert-butoxycarbonylaminomethylbenzonitrile (1.38 g, 5.16 mmol; see step (vii) above), hydroxylamine hydrochloride (1.08 g, 0.0155 mol) and triethylamine (1.57 g, 0.0155 mol) in 20 mL of ethanol was stirred at room temperature for 36 h. The solvent was evaporated and the residue was partitioned between water and methylene chloride. The organic layer was washed with water, dried ($Na_2SO_4$) and evaporated. The product could be used without further purification. Yield: 1.43 g (92%).

$^1$H NMR (500 MHz, $CD_3OD$) δ 7.14 (m, 2H), 4.97 (broad, 1H), 4.84 (broad, 2H), 4.40 (broad, 2H), 1.43 (s, 9H)

(ix) Boc-Pab(2,6-diF)×HOAc

This reaction was carried out according to the procedure described by Judkins et al, Synth. Comm. (1998) 4351. Boc-Pab(2,6-diF)(OH) (1.32 g, 4.37 mmol; see step (viii) above), acetic anhydride (0.477 g, 4.68 mmol) and 442 mg of 10% Pd/C (50% moisture) in 100 mL of acetic acid was hydrogenated at 5 atm pressure for 3.5 h. The mixture was filtered through Celite, rinsed with ethanol and evaporated. The residue was freeze-dried from acetonitrile and water and a few drops of ethanol. The sub-title product could be used without further purification. Yield: 1.49 g (99%).

¹H NMR (400 MHz, CD₃OD) δ 7.45 (m, 2H), 4.34 (s, 2H), 1.90 (s, 3H), 1.40 (s, 9H)

(x) Boc-Pab(2,6-diF)(Teoc)

To a solution of Boc-Pab(2,6-diF)×HOAc (1.56 g, 5.49 mmol; see step (ix) above) in 100 mL of THF and 1 mL of water was added 2-(trimethylsilyl)ethyl p-nitrophenyl carbonate (1.67 g, 5.89 mmol). A solution of potassium carbonate (1.57 g, 0.0114 mol) in 20 mL of water was added dropwise over 5 min. The mixture was stirred overnight. The THF was evaporated and the residue was partitioned between water and methylene chloride. The aqueous layer was extracted with methylene chloride and the combined organic phase was washed twice with aqueous sodium bicarbonate, dried (Na₂SO₄) and evaporated. Flash chromatography on silica gel with heptane/EtOAc=2/1 gave 1.71 g (73%) of pure compound.

¹H NMR (400 MHz, CDCl₃) δ 7.43 (m, 2H), 4.97 (broad, 1H), 4.41 (broad, 2H), 4.24 (m, 2H), 1.41 (s, 9H), 1.11 (m, 2H), 0.06 (s, 9H)

(xi) Boc-Aze-Pab(2,6-diF)(Teoc)

Boc-Pab(2,6-diF)(Teoc) (1.009 g, 2.35 mmol; see step (x) above) was dissolved in 50 mL of EtOAc saturated with HCl(g). The mixture was left for 10 min., evaporated and dissolved in 18 mL of DMF, and then cooled on an ice bath. Boc-Aze-OH (0.450 g, 2.24 mmol), PyBOP (1.24 g, 2.35 mmol) and lastly diisopropylethyl amine (1.158 g, 8.96 mmol) were added. The reaction mixture was stirred for 2 h and then poured into 350 mL of water and extracted three times with EtOAc. The combined organic phase was washed with brine, dried (Na₂SO₄) and evaporated. Flash chromatography on silica gel with heptane:EtOAc (1:3) gave 1.097 g (96%) of the desired compound.

¹H NMR (500 MHz, CDCl₃) δ 7.46 (m, 2H), 4.65-4.5 (m, 3H), 4.23 (m, 2H), 3.87 (m, 1H), 3.74 (m, 1H), 2.45-2.3 (m, 2H), 1.40 (s, 9H), 1.10 (m, 2H), 0.05 (s, 9H)

(xii) Ph(3-Cl)(5-OCHF₂)—(R)CH(OH)C(O)-Aze-Pab(2,6-diF)(Teoc)

Boc-Aze-Pab(2,6-diF)(Teoc) (0.256 g, 0.500 mmol; see step (xi) above) was dissolved in 20 mL of EtOAc saturated with HCl(g). The mixture was left for 10 min. and evaporated and dissolved in 5 mL of DMF. Ph(3-Cl)(5-OCHF₂)—(R)CH(OH)C(O)OH (0.120 g, 0.475 mmol; see Preparation A(viii) above), PyBOP (0.263 g, 0.498 mmol) and lastly diisopropylethyl amine (0.245 g, 1.89 mmol) were added. The reaction mixture was stirred for 2 h and then poured into 350 mL of water and extracted three times with EtOAc. The combined organic phase was washed with brine, dried (Na₂SO₄) and evaporated. Flash chromatography on silica gel with EtOAc gave 0.184 g (60%) of the desired sub-title compound.

¹H NMR (400 MHz, CD₃OD, mixture of rotamers) δ 7.55-7.45 (m, 2H), 7.32 (m, 1H, major rotamer), 7.27 (m, 1H, minor rotamer), 7.2-7.1 (m, 2H), 6.90 (t, 1H, major rotamer), 6.86 (t, 1H, minor rotamer), 5.15 (s, 1H, major rotamer), 5.12 (m, 1H, minor rotamer), 5.06 (s, 1H, minor rotamer), 4.72 (m, 1H, major rotamer), 4.6-4.45 (m, 2H), 4.30 (m, 1H, major rotamer), 4.24 (m, 2H), 4.13 (m, 1H, major rotamer), 4.04 (m, 1H, minor rotamer), 3.95 (m, 1H, minor rotamer), 2.62 (m, 1H, minor rotamer), 2.48 (m, 1H, major rotamer), 2.22 (m, 1H, major rotamer), 2.10 (m, 1H, minor rotamer), 1.07 (m, 2H), 0.07 (m, 9H)

(xiii) Ph(3-Cl)(5-OCHF₂)—(R)CH(OH)C(O)-Aze-Pab(2,6-diF)(OMe,Teoc)

A mixture of Ph(3-Cl)(5-OCHF₂)—(R)CH(OH)C(O)-Aze-Pab(2,6-diF)(Teoc) (64 mg, 0.099 mmol; see step (xii) above) and O-methyl hydroxylamine hydrochloride (50 mg, 0.60 mmol) in 4 mL of acetonitrile was heated at 70° C. for 3 h. The solvent was evaporated and the residue was partitioned between water and EtOAc. The aqueous layer was extracted twice with EtOAc and the combined organic phase was washed with water, dried (Na₂SO₄) and evaporated. The product could be used without further purification. Yield: 58 mg (87%).

¹H NMR (400 MHz, CDCl₃) δ 7.90 (bt, 1H), 7.46 (m, 1H), 7.25-6.95 (m, 5H), 6.51, t, 1H), 4.88 (s, 1H), 4.83 (m, 1H), 4.6-4.5 (m, 2H), 4.4-3.9 (m, 4H), 3.95 (s, 3H), 3.63 (m, 1H), 2.67 (m, 1H), 2.38 (m, 1H), 1.87 (broad, 1H), 0.98 (m, 2H), 0.01, s, 9H)

(xiv) Compound B

Ph(3-Cl)(5-OCHF₂)—(R)CH(OH)C(O)-Aze-Pab(2,6-diF)(OMe,Teoc) (58 mg, 0.086 mmol; see step (xiii) above) was dissolved in 3 mL of TFA, cooled on an ice bath and allowed to react for 2 h. The TFA was evaporated and the residue dissolved in EtOAc. The organic layer was washed twice with aqueous sodium carbonate and water, dried (Na₂SO₄) and evaporated. The residue was freeze-dried from water and acetonitrile to give 42 mg (92%) of the title compound.

¹H NMR (300 MHz, CDCl₃) δ 7.95 (bt, 1H), 7.2-7.1 (m, 4H), 6.99 (m, 1H), 6.52 (t, 1H), 4.88 (s, 1H), 4.85-4.75 (m, 3H), 4.6-4.45 (m, 2H), 4.29 (broad, 1H), 4.09 (m, 1H), 3.89 (s, 3H), 3.69 (m, 1H), 2.64 (m, 1H), 2.38 (m, 1H), 1.85 (broad, 1H)

¹³C-NMR (100 MHz; CDCl₃): (carbonyl and/or amidine carbons) δ 172.1, 169.8, 151.9

APCI-MS: (M+1)=533/535 m/z

Preparation C: Preparation of Compound C (i) (2-Monofluoroethyl)methanesulfonate To a magnetically stirred solution of 2-fluoroethanol (5.0 g, 78.0 mmol) in CH₂Cl₂ (90 mL) under nitrogen at 0° C. was added triethylamine (23.7 g, 234 mmol) and methanesulfonyl chloride (10.7 g, 93.7 mmol). The mixture was stirred at 0° C. for 1.5 h, diluted with CH₂Cl₂ (100 mL) and washed with 2N HCl (100 mL). The aqueous layer was extracted with CH₂Cl₂ (50 mL) and the combined organic extracts washed with brine (75 mL), dried (Na₂SO₄), filtered and concentrated in vacuo to afford the sub-title compound (9.7 g, 88%) as a yellow oil which was used without further purification.

¹H NMR (300 MHz, CDCl₃) δ 4.76 (t, J=4 Hz, 1H), 4.64 (t, J=4 Hz, 1H), 4.52 (t, J=4 Hz, 1H), 4.43 (t, J=4 Hz, 1H), 3.09 (s, 3H).

(ii) 3-Chloro-5-monofluoroethoxybenzaldehyde

To a solution of 3-chloro-5-hydroxybenzaldehyde (8.2 g, 52.5 mmol; see Preparation A(ii) above) and potassium carbonate (9.4 g, 68.2 mmol) in DMF (10 mL) under nitrogen was added a solution of (2-monofluoroethyl) methanesulfonate (9.7 g, 68.2 mmol; see step (i) above) in DMF (120 mL) dropwise at room temperature. The mixture was heated to 100° C. for 5 h and then stirred overnight at room temperature. The reaction was cooled to 0° C., poured into ice-cold 2N HCl and extracted with EtOAc. The combined organic extracts were washed with brine, dried ($Na_2SO_4$), filtered and concentrated in vacuo. The brown oil was chromatographed on silica gel eluting with Hex:EtOAc (4:1) to afford the sub-title compound (7.6 g, 71%) as a yellow oil.

$^1$H NMR (300 MHz, $CDCl_3$) δ 9.92 (s, 1H), 7.48 (s, 1H), 7.32 (s, 1H), 7.21 (s, 1H), 4.87 (t, J=4 Hz, 1H), 4.71 (t, J=3 Hz, 1H), 4.33 (t, J=3 Hz, 1H), 4.24 (t, J=3 Hz, 1H).

(iii) Ph(3-Cl)(5-OCH$_2$CH$_2$F)—(R,S)CH(OTMS)CN

To a solution of 3-chloro-5-monofluoroethoxybenzaldehyde (7.6 g, 37.5 mmol; see step (ii) above) and zinc iodide (3.0 g, 9.38 mmol) in $CH_2Cl_2$ (310 mL) was added trimethylsilyl cyanide (7.4 g, 75.0 mmol) dropwise at 0° C. under nitrogen. The mixture was stirred at 0° C. for 3 h and at room temperature overnight. The reaction was diluted with $H_2O$ (300 mL), the organic layer was separated, dried ($Na_2SO_4$), filtered and concentrated in vacuo to afford the sub-title compound (10.6 g, 94%) as a brown oil that was used without further purification or characterisation.

(iv) Ph(3-Cl)(5-OCH$_2$CH$_2$F)—(R,S)CH(OH)C(O)OH

Concentrated hydrochloric acid (100 mL) was added to Ph(3-Cl)(5-OCH$_2$CH$_2$F)—(R,S)CH(OTMS)CN (10.6 g, 5.8 mmol; see step (iii) above) and the solution stirred at 100° C. for 3 h. After cooling to room temperature, the reaction was further cooled to 0° C., basified slowly with 3N NaOH (~300 mL) and washed with $Et_2O$ (3×200 mL). The aqueous layer was acidified with 2N HCl (80 mL) and extracted with EtOAc (3×300 mL). The combined EtOAc extracts were dried ($Na_2SO_4$), filtered and concentrated in vacuo to afford the sub-title compound (8.6 g, 98%) as a pale yellow solid that was used without further purification.

$R_f$=0.28 (90:8:2 $CHCl_3$:MeOH:concentrated $NH_4OH$)

$^1$H NMR (300 MHz, $CD_3OD$) δ 7.09 (s, 1H), 7.02 (s, 1H), 6.93 (s, 1H), 5.11 (s, 1H), 4.77-4.81 (m, 1H), 4.62-4.65 (m, 1H), 4.25-4.28 (m, 1H), 4.15-4.18 (m, 1H).

(v) Ph(3-Cl)(5-OCH$_2$CH$_2$F)—(S)CH(OAc)C(O)OH (a) and Ph(3-Cl)(5-OCH$_2$CH$_2$F)—(R)CH(OH)C(O)OH (b)

A solution of Ph(3-Cl)(5-OCH$_2$CH$_2$F)—(R,S)CH(OH)C(O)OH (8.6 g, 34.5 mmol; see step (iv) above) and Lipase PS "Amano" (4.0 g) in vinyl acetate (250 mL) and MTBE (250 mL) was heated at 70° C. under nitrogen for 3 d. The reaction was cooled to room temperature and the enzyme removed by filtration through Celite®. The filter cake was washed with EtOAc and the filtrate concentrated in vacuo. Chromatography on silica gel eluting with $CHCl_3$:MeOH:$Et_3$N (90:8:2) afforded the triethylamine salt of sub-title compound (a) as a yellow oil. In addition, the triethylamine salt of sub-title compound (b) (4.0 g) was obtained. The salt of sub-title compound (b) was dissolved in $H_2O$ (250 mL), acidified with 2N HCl and extracted with EtOAc (3×200 mL). The combined organic extracts were dried ($Na_2SO_4$), filtered and concentrated in vacuo to yield the sub-title compound (b) (2.8 g, 32%) as a yellow oil.

Data for Sub-Title Compound (b):

$R_f$=0.28 (90:8:2 $CHCl_3$:MeOH:concentrated $NH_4OH$)

$^1$H NMR (300 MHz, $CD_3OD$) δ 7.09 (s, 1H), 7.02 (s, 1H), 6.93 (s, 1H), 5.11 (s, 1H), 4.77-4.81 (m, 1H), 4.62-4.65 (m, 1H), 4.25-4.28 (m, 1H), 4.15-4.18 (m, 1H).

(vi) Compound C

To a solution of Ph(3-Cl)(5-OCH$_2$CH$_2$F)—(R)CH(OH)C(O)OH (818 mg, 3.29 mmol; see step (v) above) in DMF (30 mL) under nitrogen at 0° C. was added HAze-Pab(OMe).2HCl (1.43 g, 4.27 mmol, see international patent application WO 00/42059), PyBOP (1.89 g, 3.68 mmol), and DIPEA (1.06 g, 8.23 mmol). The reaction was stirred at 0° C. for 2 h and then at room temperature overnight. The mixture was concentrated in vacuo and the residue chromatographed two times on silica gel, eluting first with $CHCl_3$:EtOH (15:1) and second with EtOAc:EtOH (20:1) to afford the title compound (880 mg, 54%).

$R_f$=0.60 (10:1 $CHCl_3$:EtOH)

$^1$H NMR (300 MHz, $CD_3OD$, complex mixture of rotamers) δ 7.58-7.60 (d, J=8 Hz, 2H), 7.34 (d, J=7 Hz, 2H), 7.05-7.08 (m, 2H), 6.95-6.99 (m, 1H), 5.08-5.13 (m, 1H), 4.77-4.82 (m, 1H), 4.60-4.68 (m, 1H), 3.99-4.51 (m, 7H), 3.82 (s, 3H), 2.10-2.75 (m, 2H).

$^{13}$C-NMR (150 MHz; $CD_3OD$): (carbonyl and/or amidine carbons) δ 173.3, 170.8, 152.5.

APCI-MS: (M+1)=493 m/z.

Preparation of Compound D Ph(3-Cl)(5-OCHF$_2$)—(R)CH(OH)C(O)-Aze-Pab

Compound D

Ph(3-Cl)(5-OCHF$_2$)—(R)CH(OH)C(O)-Aze-Pab(Teoc) (0.045 g, 0.074 mmol; see Preparation A (ix) above), was dissolved in 3 mL of TFA and allowed to react for 1 h. TFA was evaporated and the residue was freeze dried from water/acetonitrile to yield 0.043 g (100%) of the sub-title compound as its TFA salt.

$^1$H-NMR (400 MHz; $CD_3OD$) rotamers: δ 7.8-7.75 (m, 2H), 7.55-7.5 (m, 2H), 7.35 (m, 1H, major rotamer), 7.31 (m, 1H, minor rotamer), 7.19 (m, 1H, major rotamer), 7.15 (m, 1H), 7.12 (m, 1H, minor rotamer), 6.89 (t, 1H, major rotamer), 6.87 (t, 1H, minor rotamer), 5.22 (m, 1H, minor rotamer), 5.20 (s, 1H, major rotamer), 5.13 (s, 1H, minor rotamer), 4.80 (m, 1H, major rotamer), 4.6-4.4 (m, 2H), 4.37 (m, 1H, major rotamer), 4.19 (m, 1H, major rotamer), 4.07 (m, 1H, minor rotamer), 3.98 (m, 1H, minor rotamer), 2.70 (m, 1H, minor rotamer), 2.55 (m, 1H, major rotamer), 2.29 (m, 1H, major rotamer), 2.15 (m, 1H, minor rotamer)

$^{13}$C-NMR (100 MHz; $CD_3OD$): (carbonyl and/or amidine carbons, rotamers) δ 172.6, 172.5, 172.0, 171.7, 167.0

MS (m/z) 465 (M−1)$^−$, 467 (M+1)$^+$

Preparation of Compound E Ph(3-Cl)(5-OCHF$_2$)—(R)CH(OH)C(O)-Aze-Pab(2,6-diF)

Compound E

Ph(3-Cl)(5-OCHF$_2$)—(R)CH(OH)C(O)-Aze-Pab(2,6-diF)(Teoc) (81 mg, 0.127 mmol; see Preparation B (xii) above) was dissolved in 0.5 mL of methylene chloride and cooled on an ice bath. TFA (3 mL) was added and the reaction was left for 75 min. The TFA was evaporated and the residue was freeze dried from water and acetonitrile. The crude product was purified by preparative RPLC with $CH_3CN$:0.1M $NH_4OAc$ (35:65) to produce 39 mg (55%) of the title compound as its HOAc salt, purity: 99%.

$^1$H NMR (400 MHz, $CD_3OD$ mixture of rotamers) δ 7.5-7.4 (m, 2H), 7.32 (m, 1H, major rotamer), 7.28 (m, 1H, minor rotamer), 7.2-7.1 (m, 3H) 6.90 (t, 1H, major rotamer), 6.86 (t, minor rotamer), 5.15 (s, 1H, major rotamer), 5.14 (m, 1H, minor rotamer), 5.07 (s, 1H, minor rotamer), 4.72 (m, 1H, major rotamer), 4.65-4.45 (m, 2H), 4.30 (m, 1H, major rotamer), 4.16 (m, 1H, major rotamer), 4.03 (m, 1H, minor rotamer), 3.95 (m, 1H, minor rotamer), 2.63 (m, 1H, minor rotamer), 2.48 (m, 1H, major rotamer), 2.21 (m, 1H, major rotamer), 2.07 (m, 1H, minor rotamer), 1.89 (s, 3H)

$^{13}$C-NMR (75 MHz; CD$_3$OD): (carbonyl and/or amidine carbons, mixture of rotamers) δ 171.9, 171.2, 165.0, 162.8, 160.4

APCI-MS: (M+1)=503/505 m/z.

Preparation of Compound F Ph(3-Cl)(5-OCH$_2$CH$_2$F)—(R)CH(OH)C(O)-Aze-Pab×TFA (i) Ph(3-Cl)(5-OCH$_2$CH$_2$F)—(R)CH(OH)C(O)-Aze-Pab(Teoc)

To a solution of Ph(3-Cl)(5-OCH$_2$CH$_2$F)—(R)CH(OH)C(O)OH (940 mg, 3.78 mmol; see Preparation C (v) above) in DMF (30 mL) under nitrogen at 0° C. was added HAze-Pab (Teoc).HCl (2.21 g, 4.91 mmol), PyBOP (2.16 g, 4.15 mmol), and DIPEA (1.22 g, 9.45 mmol). The reaction was stirred at 0° C. for 2 h and then at room temperature for 4 h. The mixture was concentrated in vacuo and the residue chromatographed twice on silica gel, eluting first with CHCl$_3$:EtOH (15:1) and second with EtOAc:EtOH (20:1) to afford the sub-title compound (450 mg, 20%) as a crushable white foam.

Mp: 80-88° C.

R$_f$=0.60 (10:1 CHCl$_3$:EtOH)

$^1$H NMR (300 MHz, CD$_3$OD, complex mixture of rotamers) δ 7.79 (d, J=8 Hz, 2H), 7.42 (d, J=8 Hz, 2H), 7.05-7.08 (m, 1H), 6.93-6.99 (m, 2H), 5.08-5.13 (m, 1H), 4.75-4.80 (m, 2H), 4.60-4.68 (m, 1H), 3.95-4.55 (m, 8H), 2.10-2.75 (m, 2H), 1.05-1.11 (m, 2H), 0.08 (s, 9H).

APCI-MS: (M+1)=607 m/z.

(ii) Compound F

Ph(3-Cl)(5-OCH$_2$CH$_2$F)—(R)CH(OH)C(O)-Aze-Pab(Teoc) (0.357 g, 0.589 mmol; see step (i) above), was dissolved in 10 mL of TFA and allowed to react for 40 min. TFA was evaporated and the residue was freeze dried from water/acetonitrile to yield 0.33 g (93%) of the title compound as its TFA salt.

$^1$H-NMR (600 MHz; CD$_3$OD) rotamers: δ 7.8-7.7 (m, 2H), 7.54 (d, 2H), 7.08 (s, 1H, major rotamer), 7.04 (s, 1H, minor rotamer), 6.99 (s, 1H, major rotamer), 6.95 (s, 1H), 6.92 (s, 1H, minor rotamer), 5.18 (m, 1H, minor rotamer), 5.14 (s, 1H, major rotamer), 5.08 (s, 1H, minor rotamer), 4.80 (m, 1H, major rotamer), 4.73 (m, 1H), 4.65 (m, 1H), 4.6-4.4 (m, 2H), 4.35 (m, 1H, major rotamer), 4.21 (doublet of multiplets, 2H), 4.12 (m, 1H, major rotamer), 4.06 (m, 1H, minor rotamer), 3.99 (m, 1H, minor rotamer), 2.69 (m, 1H, minor rotamer), 2.53 (m, 1H, major rotamer), 2.29 (m, 1H, major rotamer), 2.14 (m, 1H, minor rotamer).

$^{13}$C-NMR (150 MHz; CD$_3$OD): (carbonyl and/or amidine carbons) δ 172.8, 172.1, 167.4.

ESI-MS+: (M+1)=463 (m/z)

Preparation of Compound G Ph(3-Cl)(5-OCHF$_2$)—(R)CH(OH)C(O)-Aze-Pab(OH)

(i) Ph(3-Cl)(5-OCHF$_2$)—(R)CH(OH)C(O)-Aze-Pab(OH, Teoc)

Ph(3-Cl)(5-OCHF$_2$)—(R)CH(OH)C(O)-Aze-Pab(Teoc) (0.148 g, 0.24 mmol; see Preparation A step (ix) above), was dissolved in 9 mL of acetonitrile and 0.101 g (1.45 mmol) of hydroxylamine hydrochloride was added. The mixture was heated at 70° C. for 2.5 h, filtered through Celite® and evaporated. The crude product (0.145 g; 75% pure) was used directly in the next step without further purification.

(ii) Ph(3-Cl)(5-OCHF$_2$)—(R)CH(OH)C(O)-Aze-Pab(OH)

Ph(3-Cl)(5-OCHF$_2$)—(R)CH(OH)C(O)-Aze-Pab(OH, Teoc) (0.145 g, 0.23 mmol; see step (i) above), was dissolved in 0.5 mL of CH$_2$Cl$_2$ and 9 mL of TFA. The reaction was allowed to proceed for 60 minutes. TFA was evaporated and the residue was purified using preparative HPLC. The fractions of interest were pooled and freeze-dried (2×), yielding 72 mg (yield over two steps 62%) of the title compound.

MS (m/z) 482 (M−1)$^-$; 484 (M+1)$^+$ $^1$H-NMR (400 MHz; CD$_3$OD): δ 7.58 (d, 2H), 7.33 (m, 3H), 7.15 (m, 2H), 6.89 (t, 1H major rotamer), 6.86 (t, 1H minor rotamer), 5.18 (s, 1H major rotamer; and m, 1H minor rotamer), 5.12 (s, 1H minor rotamer), 4.77 (m, 1H major rotamer), 4.42 (m, 2H), 4.34 (m, 1H major rotamer), 4.14 (m, 1H major rotamer), 4.06 (m, 1H minor rotamer), 3.95 (m, 1H minor rotamer), 2.66 (m, 1H minor rotamer), 2.50 (m, 1H major rotamer), 2.27 (m, 1H major rotamer), 2.14 (m, 1H minor rotamer)

$^{13}$C-NMR (100 MHz; CD$_3$OD): (carbonyl and/or amidine carbons, rotamers) δ 172.4, 172.3, 172.0, 171.4 152.3, 152.1

Preparation of Compound H: Ph(3-Cl)(5-OCHF$_2$)—(R)CH(OH)C(O)—(S)Aze-Pab(2,6-diF)(OH)

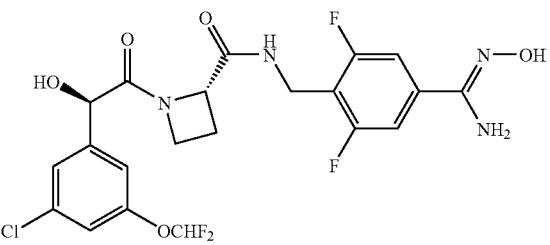

(i) Boc-(S)Aze-NHCH$_2$—Ph(2,6-diF, 4-CN)

Boc-(S)Aze-OH (1.14 g, 5.6 mmol) was dissolved in 45 mL of DMF. 4-Aminomethyl-2,6-difluorobenzonitrile (1.00 g, 5.95 mol, see Example 1(xiv) above), PyBOP (3.10 g, 5.95 mmol) and DIPEA (3.95 mL, 22.7 mmol) were added and the solution was stirred at room temperature for 2 h. The solvent was evaporated and the residue was partitioned between H$_2$O and EtOAc (75 mL each). The aqueous phase was extracted with 2×50 mL EtOAc and the combined organic phase was washed with brine and dried over Na$_2$SO$_4$. Flash chromatography (SiO$_2$, EtOAc/heptane (3/1)) yielded the sub-title compound (1.52 g, 77%) as an oil which crystallized in the refrigerator.

$^1$H-NMR (400 MHz; CD$_3$OD): δ 7.19 (m, 2H), 4.65-4.5 (m, 3H), 3.86 (m, 1H), 3.73 (m, 1H), 2.45-2.3 (m, 2H), 1.39 (s, 9H)

(ii) H—(S)Aze-NHCH$_2$—Ph(2,6-diF, 4-CN)×HCl

Boc-(S)Aze-NHCH$_2$—Ph(2,6-diF, 4-CN) (0.707 g, 2.01 mmol, see step (i) above) was dissolved in 60 mL of EtOAc saturated with HCl(g). After stirring at room temperature for 15 minutes, the solvent was evaporated. The residue was dissolved in CH$_3$CN/H$_2$O (1/1) and was freeze-dried to give the sub-title compound (0.567 g, 98%) as an off-white amorphous powder.

¹H-NMR (400 MHz; CD₃OD): δ 7.49 (m, 2H), 4.99 (m, 1H), 4.58 (m, 2H), 4.12 (m, 1H), 3.94 (m, 1H), 2.80 (m, 1H), 2.47 (m, 1H)
MS (m/z) 252.0 (M+1)⁺

(iii) Ph(3-Cl)(5-OCHF₂)—(R)CH(OH)C(O)—(S)Aze-NHCH₂—Ph(2,6-diF, 4-CN)

Ph(3-Cl)(5-OCHF₂)—(R)CH(OH)C(O)OH (0.40 g, 1.42 mmol, see Example 1(viii) above) was dissolved in 10 mL of DMF and H—(S)Aze-NHCH₂—Ph(2,6-diF, 4-CN)×HCl (0.43 g, 1.50 mmol, see step (ii) above) and PyBOP (0.779 g, 1.50 mmol) were added, followed by DIPEA (1.0 mL, 5.7 mmol). After stirring at room temperature for 2 h, the solvent was evaporated. The residue was partitioned between H₂O (200 mL) and EtOAc (75 mL). The aqueous phase was extracted with 2×75 mL EtOAc and the combined organic phase was washed with brine and dried over Na₂SO₄. Flash chromatography (SiO₂, EtOAc/heptane (4/1)) yielded the sub-title compound (0.56 g, 81%) as an oil.
¹H-NMR (400 MHz; CD₃OD) rotamers: δ 7.43 (m, 2H), 7.31 (m, 1H, major rotamer), 7.26 (m, 1H, minor rotamer), 7.2-7.1 (m, 2H), 6.90 (t, 1H, major rotamer), 6.86 (t, 1H, minor rotamer), 5.14 (s, 1H, major rotamer), 5.11 (m, 1H, minor rotamer), 5.04 (s, 1H, minor rotamer), 4.71 (m, 1H, major rotamer), 4.6-4.45 (m, 2H), 4.30 (m, 1H, major rotamer), 4.2-3.9 (m, 1H; and 1H, minor rotamer), 2.62 (m, 1H, minor rotamer), 2.48 (m, 1H, major rotamer), 2.21 (m, 1H, major rotamer), 2.09 (m, 1H, minor rotamer)
¹³C-NMR (100 MHz; CD₃OD): (carbonyl carbons) δ 171.9, 171.8 MS (m/z) 484.0, 485.9 (M−1)⁻, 486.0, 487.9 (M+1)⁺

(iv) Ph(3-Cl)(5-OCHF₂)—(R)CH(OH)C(O)—(S)Aze-Pab(2,6-diF)(OH)

Ph(3-Cl)(5-OCHF₂)—(R)CH(OH)C(O)—(S)Aze-NHCH₂—Ph(2,6-diF, 4-CN) (0.555 g, 1.14 mmol, from step (iii) above) was dissolved in 10 mL of EtOH (95%). To this solution was added hydroxylamine hydrochloride (0.238 g, 3.42 mmol) and Et₃N (0.48 mL, 3.44 mmol). After stirring at room temperature for 14 h, the solvent was removed and the residue was dissolved in EtOAc. The organic phase was washed with brine and H₂O and was dried over Na₂SO₄. The crude product was purified by preparative RPLC with CH₃CN:0.1 M NH₄OAc as eluent, yielding the title compound as an amorphous powder (0.429 g, 72%) after freeze-drying.
¹H-NMR (400 MHz; CD₃OD) rotamers: δ 7.35-7.1 (m, 5H), 6.90 (t, 1H, major rotamer), 6.85 (t, 1H, minor rotamer), 5.15 (s, 1H, major rotamer), 5.12 (m, 1H, minor rotamer), 5.08 (s, 1H, minor rotamer), 4.72 (m, 1H, major rotamer), 4.6-4.4 (m, 2H), 4.30 (m, 1H, major rotamer), 4.12 (m, 1H, major rotamer), 4.04 (m, 1H, minor rotamer), 3.94 (m, 1H, minor rotamer), 2.62 (m, 1H, minor rotamer), 2.48 (m, 1H, major rotamer), 2.22 (m, 1H, major rotamer), 2.10 (m, 1H, minor rotamer)
¹³C-NMR (100 MHz; CD₃OD): (carbonyl and amidine carbons, rotamers) δ 172.4, 171.9, 171.0, 152.3, 151.5
MS (m/z) 517.1, 519.0 (M−1)⁻, 519.1, 521.0 (M+1)⁺

Preparation of Compound J Ph(3-Cl)(5-OCH₂CHF₂)—(R)CH(OH)C(O)-Aze-Pab(OH))

(i) Ph(3-Cl)(5-OCH₂CHF₂)—(R)CH(OH)C(O)-Aze-Pab(Z)

Boc-Aze-Pab(Z) (see international patent application WO 97/02284, 92 mg, 0.197 mmol) was dissolved in 10 mL of EtOAc saturated with HCl(g) and allowed to react for 10 min. The solvent was evaporated and the residue was mixed with Ph(3-Cl)(5-OCH₂CHF₂)—(R)CH(OH)C(O)OH (50 mg, 0.188 mmol; see Preparation C (v) above), PyBOP (109 mg, 0.209 mmol) and finally diisopropylethyl amine (96 mg, 0.75 mmol) in 2 mL of DMF. The mixture was stirred for 2 h and then poured into 50 mL of water and extracted three times with EtOAc. The combined organic phase was washed with water, dried (Na₂SO₄) and evaporated. The crude product was flash chromatographed on silica gel with EtOAc:MeOH (9:1). Yield: 100 mg (87%).
¹H NMR (300 MHz, CD₃OD mixture of rotamers) δ 7.85-7.75 (m, 2H), 7.45-7.25 (m, 7H), 7.11 (m, 1H, major rotamer), 7.08 (m, 1H, minor rotamer), 7.05-6.9 (m, 2H), 6.13 (bt, 1H), 5.25-5.05 (m, 3H), 4.77 (m, 1H, partially hidden by the CD₃OH signal), 4.5-3.9 (m, 7H), 2.64 (m, 1H, minor rotamer), 2.47 (m, 1H, major rotamer), 2.25 (m, 1H, major rotamer), 2.13 (m, 1H, minor rotamer)

(ii) Ph(3-Cl)(5-OCH₂CHF₂)—(R)CH(OH)C(O)-Aze-Pab(OH)

Hydroxylamine hydrochloride (65 mg, 0.94 mmol) and triethylamine (0.319 g, 3.16 mmol) were mixed in 8 mL of THF and sonicated for 1 h at 40° C. Ph(3-Cl)(5-OCH₂CHF₂)—(R)CH(OH)C(O)-Aze-Pab(Z) (96 mg, 0.156 mmol; see step (i) above) was added with 8 mL more of THF. The mixture was stirred at 40° C. for 4.5 days. The solvent was evaporated and the crude product was purified by preparative RPLC with CH₃CN:0.1M NH₄OAc (40:60). Yield: 30 mg (38%). Purity: 99%.
¹H NMR (300 MHz, CD₃OD, mixture of rotamers) δ 7.6-7.55 (m, 2H), 7.35-7.3 (m, 2H), 7.12 (m, 1H, major rotamer), 7.09 (m, 1H, minor rotamer), 7.05-6.9 (m, 2H), 6.15 (triplet of multiplets, 1H), 5.15 (m, 1H, minor rotamer), 5.13 (s, 1H, major rotamer), 5.08 (s, 1H, minor rotamer), 4.77 (m, 1H, major rotamer), 4.5-4.2 (m, 5H), 4.08 (m, 1H, major rotamer), 3.97 (m, 1H, minor rotamer), 2.66 (m, 1H, minor rotamer), 2.50 (m, 1H major rotamer), 2.27 (m, 1H, major rotamer), 2.14 (m, 1H, minor rotamer).
¹³C-NMR (100 MHz; CD₃OD): (carbonyl and/or amidine carbons, mixture of rotamers) δ 172.8, 172.2, 171.4, 159.1, 158.9, 154.2.
APCI-MS: (M+1)=497/499 m/z Methods 1 and 2: Preparation of Salts of Compound A Method 1: General Method for Salt Preparation The following generic method was employed to prepare salts of Compound A: 200 mg of Compound A (see Preparation A above) was dissolved in 5 mL of MeOH. To this solution was added a solution of the relevant acid (1.0 molar equivalent) dissolved in 5 mL of MeOH. After stirring for 10 minutes at room temperature, the solvent was removed by way of a rotary evaporator. The remaining solid material was re-dissolved in 8 mL of acetonitrile:H₂O (1:1). Freeze-drying afforded colorless amorphous material in each case.

Acids Employed:
(1S)-(+)-10-camphorsulfonic
malic
cyclohexylsulphamic
phosphoric
dimethylphosphoric
p-toluenesulphonic
L-lysine
L-lysine hydrochloride
saccharinic
methanesulphonic
hydrochloric Appropriate characterising data are shown in Table 1.

TABLE 1

| Salt | Mw acid | Mw salt | LRMS | δ ppm (MeOD) H18, H19, H24 (see structure at end of Method 9 below) |
|---|---|---|---|---|
| (1S)-(+)-10-camphor-sulfonate | 232.20 | 729.20 | 230.9 495.1 497.0 727.3 | 7.57, 7.68, 3.97 |
| maleate | 116.07 | 612.97 | 114.8 495.1 497.0 | 7.45, 7.64, 3.89 |
| cyclohexylsulphamate | 179.24 | 676.14 | 177.9 495.1 496.9 674.3 676.1 | 7.44, 7.64, 3.89 |
| phosphate | 97.99 | 594.89 | 495.1 497.0 593.1 | 7.37, 7.61, 3.84 |
| dimethylphosphate | 126.05 | 622.95 | 124.9 495.1 497.0 621.2 623.0 | 7.50, 7.66, 3.92 |
| p-toluenesulphonate | 172.20 | 669.10 | 170.9 495.1 497.0 | 7.54, 7.71, 3.95 |
| L-lysine | 146.19 | 643.09 | 145.0 495.1 497.0 | 7.36, 7.60, 3.83 |
| L-lysine hydrochloride | 182.65 | 679.55 | 495.1 497.0 531.1 (HC | 7.36, 7.60, 3.83 |
| saccharinate | 183.19 | 680.09 | 181.9 495.1 497.0 | 7.44, 7.64. 3.89 |
| methanesulphonate | 96.11 | 593.01 | 495.1 497.0 591.2 593.1 | 7.57, 7.68, 3.97 |
| hydrochloride | 36.46 | 533.36 | 495.1 496.9 531.1 532.5 535.2 | 7.55, 7.67, 3.95 |

All salts formed in this Method were amorphous.

Method 2

Further amorphous salts of Compound A were made using analogous techniques to those described in Method 1 above from the following acids:
hydrobromic acid (1:1 salt)
hydrochloric acid (1:1 salt)
sulphuric acid (1:0.5 salt)
1,2-ethanedisulfonic acid (1:0.5 salt)
1S-camphorsulfonic acid (1:1 salt)
(+/−)-camphorsulfonic acid (1:1 salt)
ethanesulfonic acid (1:1 salt)
nitric acid (1:1 salt)
toluenesulfonic acid (1:1 salt)
methanesulfonic acid (1:1 salt)
p-xylenesulfonic acid (1:1 salt)
2-mesitylenesulfonic acid (1:1 salt)
1,5-naphthalenesulfonic acid (1:0.5 salt)
naphthalenesulfonic acid (1:1 salt)
benzenesulfonic acid (1:1 salt)
saccharinic acid (1:1 salt)
maleic acid (1:1 salt)
phosphoric acid (1:1 salt)
D-glutamic acid (1:1 salt)
L-glutamic acid (1:1 salt)
D,L-glutamic acid (1:1 salt)
L-arginine (1:1 salt)
L-lysine (1:1 salt)
L-lysine hydrochloride (1:1 salt)
glycine (1:1 salt)
salicylic acid (1:1 salt)
tartaric acid (1:1 salt)
fumaric acid (1:1 salt)
citric acid (1:1 salt)
L-(−)-malic acid (1:1 salt)
D,L-malic acid (1:1 salt)
D-gluconic acid (1:1 salt)

Method 3

Preparation of Amorphous Compound A, Ethanesulfonic Acid Salt

Compound A (203 mg; see Preparation A above) was dissolved in ethanol (3 mL) and ethanesulfonic acid (1 eq., 95%, 35 µL) was added to the solution. The mixture was stirred for a few minutes, and then the solvent was evaporated. The resulting oil was slurried in iso-octane and evaporated to dryness until a solid material was obtained. Finally, the substance was re-slurried in iso-octane and the solvent evaporated again resulting in a white, dry, amorphous solid. The substance was vacuum dried at 40° C. overnight.

Methods 4 to 9: Preparation of Crystalline Compound A, Ethanesulfonic Acid Salt

Method 4: Crystallisation of Amorphous Material

Amorphous Compound A, ethanesulfonic acid salt (17.8 mg; see Method 3 above) was slurried in methyl iso-butyl ketone (600 µL). After 1 week, crystalline needles were observed, which were filtered off and air-dried.

Methods 5 to 7: Reaction Crystallisations (Without Anti-Solvent)

Method 5

Compound A (277 mg; see Preparation A above) was dissolved in methyl iso-butyl ketone (3.1 mL). Ethanesulfonic acid was added (1 eq., 95%, 48 µL). Precipitation of amorphous ethanesulfonate salt occurred immediately. More methyl iso-butyl ketone (6 mL) was added and the slurry was treated with ultrasound. Finally, a third portion of methyl iso-butyl ketone (3.6 mL) was added and then the slurry was left overnight with stirring (magnetic stirrer). The next day, the substance had transformed into crystalline needles. The slurry was filtered off, washed with methyl iso-butyl ketone (0.5 mL) and air dried.

Method 6

Compound A (236 mg; see Preparation A above) was dissolved at room temperature in methyl iso-butyl ketone (7 mL). Ethanesulfonic acid (1 eq., 41 µL) was mixed with 2 mL of methyl iso-butyl ketone in a vial. The solution of Compound A was seeded with crystalline Compound A, ethanesulfonic acid salt (see Methods 4 and 5 above). Then, 250 µL of the methyl iso-butyl ketone solution of ethanesulfonic acid was added in portions over 45 minutes. The solution was seeded again, and the temperature was increased to 30° C. Then, 500 μL of the methyl iso-butyl ketone solution was added over approximately 1 hour. The resulting slurry was left overnight before a final amount of the methyl iso-butyl ketone/acid solution was added over 20 minutes. The vial was rinsed with 1.5 mL of methyl iso-butyl ketone, which was added to the slurry. After a further 6 hours, the crystals were filtered off, washed with methyl iso-butyl ketone (2 mL) and dried under reduced pressure at 40° C. A total of 258 mg of crystalline salt was obtained which corresponds to a yield of approximately 87%.

Method 7

Compound A (2.36 g; see Preparation A above) was dissolved in methyl iso-butyl ketone (90 mL). Seed crystals (10 mg) of Compound A, ethanesulfonic acid salt (see Methods 4 to 6 above) were added to the solution, and then ethanesulfonic acid (40 TL) was added in two portions. Further seed crystals (12 mg) and two portions of ethanesulfonic acid (2×20 μL) were then added. The slurry was diluted with methyl iso-butyl ketone (15 mL) before the addition of ethanesulfonic acid was continued. A total amount of 330 μL ethanesulfonic acid was added, in portions, over 1 hour. A small amount of seed crystals was added and, finally, the slurry was left overnight with stirring. The next day, the crystals were filtered off, washed with methyl iso-butyl ketone (2×6 mL) and dried under reduced pressure at 40° C. After drying, a total of 2.57 g of white, crystalline product was obtained corresponding to a yield of 89%.

Methods 8 and 9: Reaction Crystallizations (With Anti-Solvent)

Method 8

Compound A (163 mg; see Preparation A above) was dissolved in iso-propanol (1.2 mL). The solution was heated to 35° C. Ethanesulfonic acid was added (28 μL). Then, ethyl acetate (4.8 mL) was added and the solution was seeded with crystalline Compound A, ethanesulphonic acid salt (see Methods 4 to 7 above). Crystallization started almost immediately. The slurry was left for about 80 minutes at 35° C. before being allowed to cool to ambient temperature (21° C.). Two hours later, the crystals were filtered off, washed three times with ethyl acetate (3×0.4 mL), and dried under reduced pressure at 40° C. A total of 170 mg of crystalline title product was obtained which corresponds to a yield of approximately 82%.

Method 9

Compound A (20.0 g; see Preparation A above) was dissolved in iso-propanol (146.6 mL) at 40° C. and ethanesulfonic acid (3.46 mL, 95%, 1 eq.) was added to the solution. To the resulting clear solution, seed crystals of Compound A, ethanesulfonic acid salt were added (50 mg; see Methods 4 to 8 above). Then, ethyl acetate (234 mL) was added over 10 minutes. The resulting slightly opaque solution was seeded once more (70 mg) and left for one hour at 40° C. with stirring to allow for crystallization to start. After this, a total of 352 mL of ethyl acetate was added at a constant rate over one hour. When all of the ethyl acetate had been added, the slurry was left for 1 hour, before being cooled to 21° C. over 2 hours. The crystallization was allowed to continue for 1 hour at 21° C. before the crystals were filtered off, washed twice with ethyl acetate (50 mL+60 mL) and finally, dried under reduced pressure at 40° C. overnight. A total of 21.6 g of a white, crystalline salt was obtained, corresponding to a yield of approximately 90%.

Compound A, ethanesulfonic acid salt was characterised by NMR as follows: 23 mg of the salt was dissolved in deuterated methanol (0.7 mL) troscopy. A combination of 1D ($^1$H, $^{13}$C and selective NOE) and 2D (gCOSY, gHSQC and gHMBC) NMR experiments were used. All data were in good agreement with the theoretical structure of the salt, shown below. The molecule exists in two conformations in methanol. Based on the integral of the peak assigned to H5 (dominant conformer) and peak assigned to H5' (other conformer), the ratio between the two conformers was found to be 70:30. H22 could not be observed as these protons were in fast exchange with the solvent $CD_3OD$.

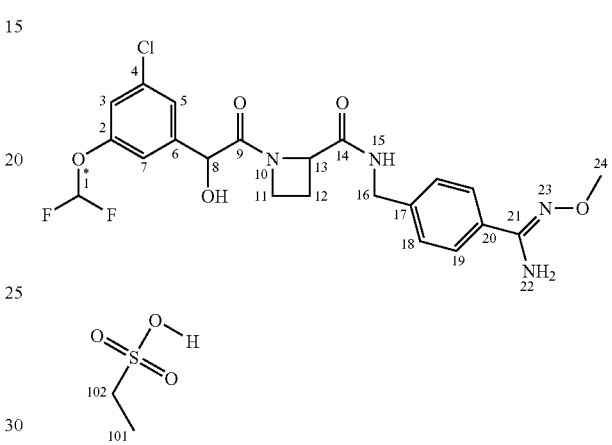

Both the proton and the carbon resonance corresponding to position 1 are split due to the spin-coupling with the two fluorine nuclei in that position. The coupling constants are $^2J_{HF}$=73 Hz and $^1J_{CF}$=263 Hz.

$^1$H and $^{13}$C NMR chemical shift assignment and proton-proton correlations are shown in Table 2.

TABLE 2

| Atom No. | Type | $^{13}$C shift/ppm$^a$ | $^1$H shift/ppm$^b$ and multiplicity$^c$ | $J_{HH}$/Hz |
|---|---|---|---|---|
| 1 | CH | 117.5$^e$ | 6.90 (t) | 73 ($^2J_{HF}$) |
| 1' | | 117.5$^e$ | 6.88 (t) | |
| 2 | C | 153.5 | | |
| 2' | | 153.5 | | |
| 3 | CH | 120.0 | 7.15 (s) | |
| 3' | | 119.7 | 7.13 (s) | |
| 4 | C | 136.2 | | |
| 4' | | 135.9 | | |
| 5 | CH | 125.0 | 7.36 (s) | |
| 5' | | 124.9 | 7.31 (s) | |
| 6 | C | 144.5 | | |
| 6' | | 145.3 | | |
| 7 | CH | 117.3 | 7.20 (s) | |
| 7' | | 117.2 | 7.15 (s) | |
| 8 | CH | 72.0 | 5.20 (s) | |
| 8' | | 74.0 | 5.12 (s) | |
| 9 | CO | 173.1 | | |
| 9' | | 173.8 | | |
| 11 | $CH_2$ | 51.6 | a: 4.38 (m)<br>b: 4.21 (m) | |
| 11' | | 49.0 | a: 4.06 (m)<br>b: 3.99 (m) | |
| 12 | $CH_2$ | 21.7 | a: 2.55 (m)<br>b: 2.29 (m) | |
| 12' | | 23.2 | a: 2.70 (m)<br>b: 2.15 (m) | |

TABLE 2-continued

| Atom No. | Type | $^{13}C$ shift/ ppm[a] | $^1H$ shift/ppm[b] and multiplicity[c] | $J_{HH}$/Hz |
|---|---|---|---|---|
| 13 | CH | 63.1 | 4.80 (m) | |
| 13' | | 66.2 | 5.22 (m) | |
| 14 | CO | 172.9 | | |
| 14' | | 173.6 | | |
| 15 | NH | | 8.76 (t, br) | 5.2 |
| 15' | | | 8.79 (t, br) | 5.2 |
| 16 | CH$_2$ | 43.5 | 4.59 (AB-pattern) | 15.9 |
| | | | 4.46 (AB-pattern) | 15.9 |
| 16' | | 43.6 | 4.53 (AB-pattern) | 15.9 |
| | | | 4.49 (AB-pattern) | 15.9 |
| 17 | C | 146.9 | | |
| 17' | | 147.0 | | |
| 18 | CH | 129.1 | 7.56 (d) | 7.8 |
| 18' | | 129.1 | 7.57 (d) | 7.8 |
| 19 | CH | 129.2 | 7.67 (d) | 7.8 |
| 19' | | 129.4 | 7.70 (d) | 7.8 |
| 20 | C | 124.9 | — | |
| 20' | | 124.9 | | |
| 21 | C | 162.4 | | |
| 21' | | 162.3 | | |
| 22 | NH$_2$ | | Not observed | |
| 24 | CH$_3$ | 64.8 | 3.96 (s) | |
| 101 | CH3 | | 1.28 (t) | 7.4 |
| 102 | CH2 | | 2.77 (m) | 7.4 |

[a]Relative to the solvent resonance at 49.0 ppm.
[b]Relative to the solvent resonance at 3.30 ppm.
[c]s = singlet, t = triplet, m = multiplet, br = broad, d = doublet
[d]Obtained in the gCOSY experiment.
[e]The resonance is a triplet due to coupling with the two fluorine nuclei. $^1J_{CF} = 263$ Hz.

HRMS calculated for $C_{24}H_{29}ClF_2N_4O_8S$ (M-H)$^-$ 605.1284, found 605.1296.

Crystals of Compound A, ethanesulfonic acid salt (obtained by way of one or more of Examples 4 to 9 above) were analyzed by XRPD and the results are tabulated below (Table 3) and are shown in FIG. 1.

TABLE 3

| d value (Å) | Intensity (%) | Intensity |
|---|---|---|
| 16.5 | 10 | m |
| 12.2 | 74 | vs |
| 11.0 | 4 | w |
| 9.0 | 33 | s |
| 8.3 | 3 | vw |
| 7.6 | 6 | w |
| 6.4 | 4 | w |
| 6.2 | 12 | m |
| 6.0 | 7 | m |
| 5.9 | 10 | m |
| 5.5 | 15 | m |
| 5.4 | 100 | vs |
| 5.1 | 7 | m |
| 4.66 | 29 | s |
| 4.60 | 36 | s |
| 4.31 | 57 | s |
| 4.25 | 18 | m |
| 4.19 | 20 | m |
| 4.13 | 12 | m |
| 4.00 | 12 | m |
| 3.87 | 13 | m |
| 3.83 | 6 | w |
| 3.76 | 7 | m |
| 3.72 | 6 | w |
| 3.57 | 9 | m |
| 3.51 | 7 | m |
| 3.47 | 5 | w |
| 3.39 | 3 | vw |
| 3.31 | 11 | m |
| 3.26 | 10 | m |
| 3.21 | 8 | m |
| 3.16 | 4 | w |
| 3.03 | 8 | m |
| 2.78 | 4 | w |
| 2.74 | 5 | w |
| 2.67 | 3 | vw |
| 2.56 | 5 | w |
| 2.50 | 5 | w |
| 2.46 | 7 | m |
| 2.34 | 4 | w |
| 2.21 | 5 | w |
| 2.00 | 3 | vw |
| 1.98 | 3 | vw |

DSC showed an endotherm with an extrapolated melting onset temperature of ca. 131° C. TGA showed a decrease in mass of ca. 0.2% (w/w) around the melting point. DSC analysis repeated with a sample of lower solvent content showed a melting onset temperature of ca. 144° C.

Method 10

Preparation of Amorphous Compound A, Benzenesulfonic Acid Salt

Compound A (199 mg; see Preparation A above) was dissolved in ethanol (2 mL). Benzenesulfonic acid (1 eq. 90%, 70 mg) was dissolved in ethanol (1 mL) in a vial. The ethanol solution of the acid was added to the solution of Compound A and the vial was rinsed with 1 mL ethanol, which was then added to the mixture. The mixture was stirred for a few minutes, and then the ethanol was evaporated until an oil was formed. Ethyl acetate (3 mL) was added and the solvent was evaporated again to dryness. An amorphous solid was formed.

Methods 11 to 13: Preparation of Crystalline Compound A, Benzenesulfonic Acid Salt Method 11: Crystallisation of Amorphous Material Amorphous Compound A benzenesulfonic acid salt (20.7 mg; see Method 10 above) was slurried in ethyl acetate (600 TL). After 5 days, crystalline needles were observed in the slurry.

Methods 12 and 13: Reaction Crystallisations

Method 12

Compound A (128 mg; see Preparation A above) was dissolved in ethyl acetate (3 mL). The solution was seeded with the slurry from Method 11 above. Then, benzenesulfonic acid was added (1 eq., 90%, 45 mg). Precipitation of benzenesulphonic acid salt occurred immediately. iso-Propanol was added to the slurry (0.8 mL) and the mixture was seeded again. Two days later, the substance had transformed into crystalline needles. The slurry was filtered off, washed with ethyl acetate (3×0.2 mL) and dried for a short time under vacuum at 40° C. A total of approximately 140 mg of white solid was obtained.

Method 13

Compound A (246 mg; see Preparation A above) was dissolved in iso-propanol (1.52 mL). Benzenesulfonic acid was added (88 mg, 90%). To the clear solution, ethyl acetate was added (3 mL), and then the mixture was seeded to initiate crystallisation. After 1 hour, more ethyl acetate was added (2.77 mL). Finally, the slurry was allowed to crystallise overnight before the crystals were filtered off, washed with ethyl acetate (3×0.3 mL) and dried at 40° C. under vacuum. A total of 279 mg salt was obtained which corresponds to a yield of approximately 86%.

Compound A, benzenesulfonic acid salt was characterised by NMR as follows: 20 mg of the salt was dissolved in deuterated methanol (0.7 mL). A combination of 1D ($^1$H, $^{13}$C and selective NOE) and 2D (gCOSY, gHSQC and gHMBC) NMR experiments were used. All data were in good agreement with the theoretical structure of the salt, shown below. The molecule exists in two conformations in methanol. Based on the integral of the peak assigned to H12 (dominant conformer) and peak assigned to H12' (other conformer), the ratio between the two conformers was found to be 70:30. H22 could not be observed as these protons were in fast exchange with the solvent $CD_3OD$.

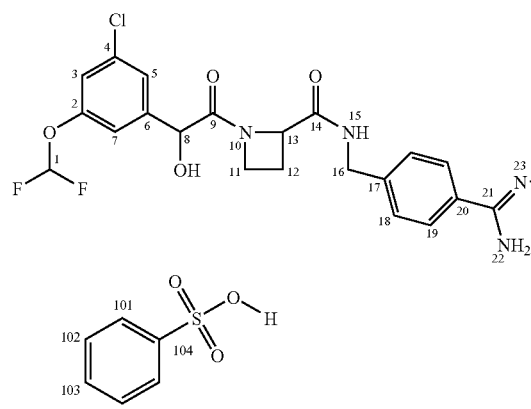

Both the proton and the carbon resonance corresponding to position 1 are split due to the spin-coupling with the two fluorine nuclei in that position. The coupling constants are $^2J_{HF}$=74 Hz and $^1J_{CF}$=260 Hz.

$^1$H and $^{13}$C NMR chemical shift assignment and proton-proton correlations are shown in Table 4.

TABLE 4

| Atom No. | Type | $^{13}$C shift/ppm$^a$ | $^1$H shift/ppm$^b$ and multiplicity$^c$ | $J_{HH}$/Hz |
|---|---|---|---|---|
| 1 | CH | 117.5$^e$ | 6.89 (t) | 74 ($^2J_{HF}$) |
| 1' |  | 117.5$^e$ | 6.87 (t) |  |
| 2 | C | 153.5 |  |  |
| 2' |  | 153.5 |  |  |
| 3 | CH | 120.1 | 7.15 (s) |  |
| 3' |  | 119.7 | 7.12 (s) |  |
| 4 | C | 136.2 |  |  |
| 4' |  | 135.9 |  |  |
| 5 | CH | 125.1 | 7.35 (s) |  |
| 5' |  | 124.9 | 7.31 (s) |  |
| 6 | C | 144.5 |  |  |
| 6' |  | 145.3 |  |  |
| 7 | CH | 117.3 | 7.20 (s) |  |
| 7' |  | 117.2 | 7.14 (s) |  |
| 8 | CH | 72.8 | 5.20 (s) |  |
| 8' |  | 74.0 | 5.12 (s) |  |
| 9 | CO | 173.1 |  |  |
| 9' |  | 173.8 |  |  |
| 11 | CH$_2$ | 51.6 | a: 4.37 (m) |  |
|  |  |  | b: 4.20 (m) |  |

TABLE 4-continued

| Atom No. | Type | $^{13}$C shift/ppm$^a$ | $^1$H shift/ppm$^b$ and multiplicity$^c$ | $J_{HH}$/Hz |
|---|---|---|---|---|
| 11' |  | 49.0 | a: 4.05 (m) |  |
|  |  |  | b: 3.98 (m) |  |
| 12 | CH$_2$ | 21.7 | a: 2.53 (m) |  |
|  |  |  | b: 2.28 (m) |  |
| 12' |  | 23.2 | a: 2.69 (m) |  |
|  |  |  | b: 2.14 (m) |  |
| 13 | CH | 63.1 | 4.79 (m) |  |
| 13' |  | 66.2 | 5.22 (m) |  |
| 14 | CO | 172.9 |  |  |
| 14' |  | 173.6 |  |  |
| 15 | NH |  | 8.75 (t, br) | 5.3 |
| 15' |  |  | 8.78 (t, br) | 5.3 |
| 16 | CH$_2$ | 43.5 | 4.59 (AB-pattern) | 16.0 and 5.2 |
|  |  |  | 4.44 (AB-pattern) | 16.0 and 4.8 |
| 16' |  | 43.6 | 4.51 (AB-pattern) | 16.0 |
|  |  |  | 4.46 (AB-pattern) | 16.0 |
| 17 | C | 146.9 |  |  |
| 17' |  | 147.0 |  |  |
| 18 | CH | 129.2 | 7.54 (d) | 8.3 |
| 18' |  | 129.2 | 7.56 (d) | 8.3 |
| 19 | CH | 129.3 | 7.66 (d) | 8.3 |
| 19' |  | 129.4 | 7.69 (d) | 8.3 |
| 20 | C | 124.9 | — |  |
| 20' |  | 124.9 |  |  |
| 21 | C | 162.4 |  |  |
| 21' |  | 162.4 |  |  |
| 22 | NH$_2$ |  | Not observed |  |
| 24 | CH$_3$ | 64.8 | 3.95 (s) |  |
| 101 | CH | 126.9 | 7.81 (m) |  |
| 102 | CH | 129.1 | 7.41 (m) |  |
| 103 | CH | 131.2 | 7.42 (m) |  |
| 104 | C | 146.4 |  |  |

$^a$Relative to the solvent resonance at 49.0 ppm.
$^b$Relative to the solvent resonance at 3.30 ppm.
$^c$s = singlet, t = triplet, m = multiplet, br = broad, d = doublet.
$^d$Obtained in the gCOSY experiment.
$^e$The resonance is a triplet due to coupling with the two fluorine nuclei. $^1J_{CF}$ = 260 Hz.
$^f$connectivity difficult to determine due to overlap between resonance 102 and 103

HRMS calculated for $C_{28}H_{29}ClF_2N_4O_8S$ (M−H)$^−$ 653.1284, found 653.1312.

Crystals of Compound A, benzenesulfonic acid salt (obtained by way of one or more of Examples 11 to 13 above) were analyzed by XRPD and the results are tabulated below (Table 5) and are shown in FIG. 2.

TABLE 5

| d value (Å) | Intensity (%) | Intensity |
|---|---|---|
| 14.2 | 12 | m |
| 12.6 | 55 | s |
| 10.2 | 49 | s |
| 7.5 | 8 | m |
| 6.4 | 5 | w |
| 6.3 | 30 | s |
| 6.1 | 5 | w |
| 5.9 | 100 | vs |
| 5.7 | 20 | m |
| 5.4 | 9 | m |
| 5.3 | 11 | m |
| 5.1 | 10 | m |
| 4.96 | 3 | vw |
| 4.83 | 27 | s |
| 4.73 | 72 | vs |
| 4.54 | 23 | s |
| 4.50 | 10 | m |
| 4.35 | 28 | s |
| 4.30 | 38 | s |
| 4.24 | 24 | s |
| 4.17 | 28 | s |
| 4.09 | 60 | vs |
| 4.08 | 61 | vs |

TABLE 5-continued

| d value (Å) | Intensity (%) | Intensity |
|---|---|---|
| 3.96 | 29 | s |
| 3.91 | 15 | m |
| 3.77 | 22 | s |
| 3.62 | 11 | m |
| 3.52 | 20 | m |
| 3.31 | 44 | s |
| 3.19 | 8 | m |
| 3.15 | 11 | m |
| 3.09 | 8 | m |
| 3.00 | 7 | m |
| 2.89 | 3 | vw |
| 2.86 | 4 | w |
| 2.79 | 7 | m |
| 2.76 | 6 | w |
| 2.72 | 5 | w |
| 2.59 | 6 | w |
| 2.56 | 9 | m |
| 2.54 | 9 | m |
| 2.49 | 7 | m |
| 2.38 | 8 | m |
| 2.16 | 4 | w |
| 2.03 | 3 | vw |

DSC showed an endotherm with an extrapolated melting onset temperature of ca. 152° C. TGA showed a decrease in mass of ca. 0.1% (w/w) around the melting point.

Method 14

Preparation of Amorphous Compound A, n-Propanesulfonic Acid Salt

Compound A (186 mg; see Preparation A above) was dissolved in iso-propanol (1.39 mL) and n-propanesulfonic acid (1 eq., 95%, 39 TL) was added. Ethyl acetate (5.6 mL) was added and the solvent was evaporated until a dry, amorphous solid was formed.

Methods 15 and 16: Preparation of Crystalline Compound A, n-Propanesulfonic Acid Salt Method 15: Crystallisation of Amorphous Material Amorphous Compound A, n-propanesulfonic acid salt (20 mg; see Method 14 above) was dissolved in iso-propanol (60 TL) and iso-propyl acetate (180 TL) was added. After three days crystalline needles were observed.

Method 16: Reaction Crystallisation

Compound A (229 mg; see Preparation A above) was dissolved in iso-propanol (1.43 mL). n-Propanesulfonic acid was added (1 eq., 95%, 48 TL). Ethyl acetate was added (2 mL), and then the solution was seeded with crystalline salt from Method 15 above. Further ethyl acetate was added (5 mL) and the slurry was left overnight to crystallize. The crystals were filtered off, washed with ethyl acetate (3×0.3 mL) and dried under vacuum at 40° C.

Compound A, n-propanesulfonic acid salt was characterised by NMR as follows: 13 mg of the salt was dissolved in deuterated methanol (0.7 mL) troscopy. A combination of 1D ($^1$H, $^{13}$C) and 2D (gCOSY) NMR experiments were used. All data were in good agreement with the theoretical structure of the salt, shown below. The molecule exists in two conformations in methanol. Based on the integral of the peak assigned to H12 (dominant conformer) and peak assigned to H12' (other conformer), the ratio between the two conformers was found to be 65:35. H22 could not be observed as these protons were in fast exchange with the solvent $CD_3OD$.

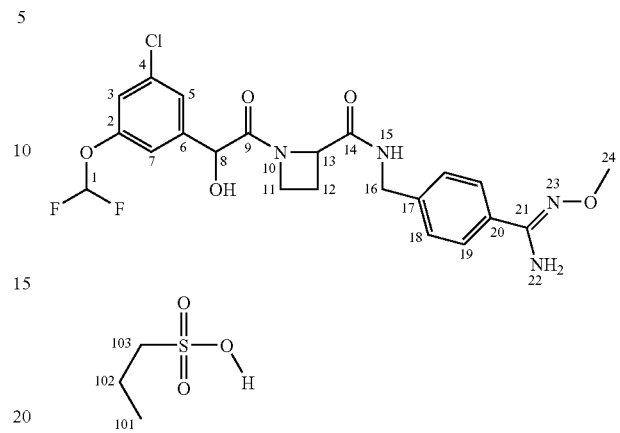

Both the proton and the carbon resonance corresponding to position 1 are split due to the spin-coupling with the two fluorine nuclei in that position. The coupling constants are $^2J_{HF}$=74 Hz and $^1J_{CF}$=260 Hz.

$^1$H and $^{13}$C NMR chemical shift assignment and proton-proton correlations are shown in Table 6.

TABLE 6

| Atom No. | Type | $^{13}$C shift/ppm$^a$ | $^1$H shift/ppm$^b$ and multiplicity$^c$ | $J_{HH}$/Hz |
|---|---|---|---|---|
| 1 | CH | 117.5$^e$ | 6.89 (t) | 74 ($^2J_{HF}$) |
| 1' | | 117.5$^e$ | 6.88 (t) | |
| 2 | C | 153.5 | | |
| 2' | | 153.5 | | |
| 3 | CH | 120.0 | 7.16 (s) | |
| 3' | | 119.7 | 7.13 (s) | |
| 4 | C | 136.2 | | |
| 4' | | 135.9 | | |
| 5 | CH | 125.1 | 7.36 (s) | |
| 5' | | 124.9 | 7.31 (s) | |
| 6 | C | 144.5 | | |
| 6' | | 145.3 | | |
| 7 | CH | 117.3 | 7.20 (s) | |
| 7' | | 117.2 | 7.16 (s) | |
| 8 | CH | 72.9 | 5.20 (s) | |
| 8' | | 74.1 | 5.12 (s) | |
| 9 | CO | 173.1 | | |
| 9' | | 173.8 | | |
| 11 | $CH_2$ | 51.6 | a: 4.37 (m) | |
| | | | b: 4.20 (m) | |
| 11' | | 49.0 | a: 4.06 (m) | |
| | | | b: 3.98 (m) | |
| 12 | $CH_2$ | 21.7 | a: 2.53 (m) | |
| | | | b: 2.29 (m) | |
| 12' | | 23.2 | a: 2.69 (m) | |
| | | | b: 2.15 (m) | |
| 13 | CH | 63.1 | 4.80 (m) | |
| 13' | | 66.2 | 5.22 (m) | |
| 14 | CO | 172.9 | | |
| 14' | | 173.8 | | |
| 15 | NH | | 8.75 (t, br) | 5.5 |
| 15' | | | 8.79 (t, br) | 5.5 |
| 16 | $CH_2$ | 43.5 | 4.59 (AB-pattern) | 16.0 and 6.6 |
| | | | 4.45 (AB-pattern) | 16.0 and 5.3 |
| 16' | | 43.6 | 4.51 | |
| | | | 4.50 | |
| 17 | C | 146.9 | | |
| 17' | | 147.0 | | |
| 18 | CH | 129.1 | 7.54 (d) | 8.5 |
| 18' | | 129.2 | 7.57 (d) | 8.5 |
| 19 | CH | 129.2 | 7.67 (d) | 8.5 |

TABLE 6-continued

| Atom No. | Type | ¹³C shift/ppm[a] | ¹H shift/ppm[b] and multiplicity[c] | $J_{HH}$/Hz |
|---|---|---|---|---|
| 19' | | 129.4 | 7.69 (d) | 8.5 |
| 20 | C | 124.9 | — | |
| 20' | | 124.9 | | |
| 21 | C | 162.4 | | |
| 21' | | 162.4 | | |
| 22 | NH₂ | | Not observed | |
| 24 | CH₃ | 64.7 | 3.96 (s) | |
| 101 | CH | 13.7 | 1.0 (t) | |
| 102 | CH | 19.6 | 1.78 (m) | |
| 103 | CH | 54.6 | 2.75 (m) | |

[a]Relative to the solvent resonance at 49.0 ppm.
[b]Relative to the solvent resonance at 3.30 ppm.
[c]s = singlet, t = triplet, m = multiplet, br = broad, d = doublet.
[d]Obtained in the gCOSY experiment.
[e]The resonance is a triplet due to coupling with the two fluorine nuclei. $^1J_{CF}$ = 260 Hz.

HRMS calculated for $C_{25}H_{31}ClF_2N_4O_8S$ (M–H)⁻ 619.1441, found 619.1436.

Crystals of Compound A, n-propanesulfonic acid salt (obtained by way of one or more of Examples 15 and 16 above) were analyzed by XRPD and the results are tabulated below (Table 7) and are shown in FIG. 3.

TABLE 7

| d value (Å) | Intensity (%) | Intensity |
|---|---|---|
| 14.0 | 4 | w |
| 12.4 | 87 | vs |
| 10.0 | 30 | s |
| 8.0 | 3 | vw |
| 7.5 | 7 | m |
| 7.0 | 0.6 | vw |
| 6.7 | 1 | vw |
| 6.4 | 1 | vw |
| 6.2 | 12 | m |
| 6.1 | 3 | vw |
| 5.8 | 100 | vs |
| 5.7 | 11 | m |
| 5.5 | 3 | vw |
| 5.4 | 5 | w |
| 5.3 | 5 | w |
| 5.2 | 2 | vw |
| 5.1 | 3 | vw |
| 4.94 | 3 | vw |
| 4.78 | 21 | s |
| 4.68 | 42 | s |
| 4.51 | 10 | m |
| 4.49 | 7 | m |
| 4.40 | 5 | w |
| 4.32 | 10 | m |
| 4.29 | 10 | m |
| 4.25 | 22 | s |
| 4.19 | 14 | m |
| 4.14 | 15 | m |
| 4.07 | 23 | s |
| 4.04 | 20 | m |
| 3.94 | 16 | m |
| 3.88 | 10 | m |
| 3.73 | 15 | m |
| 3.65 | 2 | vw |
| 3.59 | 3 | vw |
| 3.48 | 18 | m |
| 3.28 | 23 | m |
| 3.12 | 4 | w |
| 3.06 | 3 | vw |
| 2.97 | 6 | w |
| 2.84 | 2 | vw |
| 2.81 | 3 | vw |
| 2.76 | 2 | vw |
| 2.73 | 3 | vw |
| 2.70 | 2 | vw |
| 2.57 | 2 | vw |

TABLE 7-continued

| d value (Å) | Intensity (%) | Intensity |
|---|---|---|
| 2.54 | 6 | w |
| 2.51 | 6 | w |
| 2.46 | 8 | m |
| 2.42 | 2 | vw |
| 2.39 | 3 | vw |
| 2.36 | 3 | vw |
| 2.32 | 2 | vw |
| 2.14 | 3 | vw |
| 2.01 | 2 | vw |

DSC showed an endotherm with an extrapolated melting onset temperature of ca. 135° C. TGA showed no decrease in mass around the melting point.

Method 17

Method 17-A: Preparation of Amorphous Compound A n-Butane Sulfonic Acid Salt

Amorphous Compound A (277 mg) was dissolved in IPA (1.77 ml) and butane sulfonic acid (approx. 1 eq. 70 μL) was added. Ethyl acetate (6 ml) was added and the solvent was evaporated until dry, amorphous solid was formed.

Method 17-B: Preparation of Crystalline Compound A Butane Sulfonic Acid Salt

Amorphous Compound A butane sulfonic acid salt (71.5 mg; see preparation above) was slurried in ethyl acetate (500 μl) over night. The crystals were filtered off and were air-dried.

Compound A, butanesulfonic acid salt was characterised by NMR as follows: 21.6 mg of the salt was dissolved in deuterated dimethylsulfoxide (0.7 ml) and was investigated with ¹H and ¹³C NMR spectroscopy.

The spectra are very similar to other salts of the same compound and in good agreement with the structure shown below. Most resonances in the spectra are present as sets of two peaks due to the slow rotation around the C9-N10 bond, which results in two atropisomers that simultaneously exist in the solution. This is shown for other salts of the same compound.

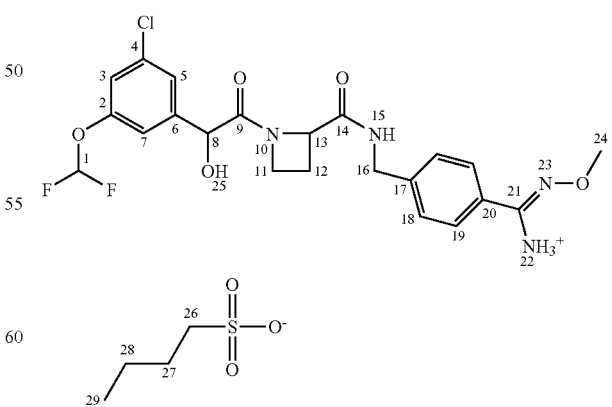

The two fluorine nuclei in position 1 give rise to split resonances for the proton and the carbon in that position. The coupling constants are $^2J_{HF}$=73 HZ and $^1J_{CF}$=258 Hz.

Chemical shifts for protons and carbons are presented in Table 1. Protons in position 22 and 24 are not detected due to chemical exchange. There is a very broad hump between 8 and 9 ppm in the proton spectrum corresponding to these protons.

TABLE 8

$^1$H and $^{13}$C NMR chemical shift assignment of Compound A n-butanesulfonate salt in deuterated dimethylsulfoxide at 25° C.

| Atom No. | Type | $^{13}$C shift/ppm$^a$ | $^1$H shift/ppm$^b$ and multiplicity$^c$ | $J_{HH}$/Hz |
|---|---|---|---|---|
| 1 | CHF$_2$ | 116.3$^d$ | 7.29 (t) | 73 ($^2J_{HF}$) |
| 1' |  | 116.3$^d$ | 7.28 (t) | 73 ($^2J_{HF}$) |
| 2 | C | 151.5 | na | na |
| 2' |  | 151.3 | na | na |
| 3 | CH | 118.0 | 7.25 (t)$^e$ | nd |
| 3' |  | 117.6 | 7.21 (t)$^e$ | nd |
| 4 | C | 133.8 | na | na |
| 4' |  | 133.4 | na | na |
| 5 | CH | 123.8 | 7.34 (t)$^e$ | nd |
| 5' |  | 123.6 | 7.25 (t)$^e$ | nd |
| 6 | C | 144.5 | na | na |
| 6' |  | 145.2 | na | na |
| 7 | CH | 116.3 | 7.19 (t)$^e$ | nd |
| 7' |  | 116.1 | 7.12 (t)$^e$ | nd |
| 8 | CH | 70.9 | 5.13 (s) | na |
| 8' |  | 71.2 | 4.99 (s) | na |
| 9 | CO | 170.6 | na | na |
| 9' |  | 171.1 | na | na |
| 11 | CH$_2$ | 50.0 | a: 4.24 (m) b: 4.12 (m) | nd |
| 11' |  | 46.9 | 3.85 (m) | nd |
| 12 | CH$_2$ | 20.5 | a: 2.41 (m) b: 2.10 (m) | nd |
| 12' |  | 21.7 | a: 2.60 (m) b: 2.02 (m) | nd |
| 13 | CH | 61.2 | 4.65 (dd) | 5.6 and 8.9 |
| 13' |  | 63.9 | 5.12 (m) | nd |
| 14 | CO | 170.2 | na | na |
| 14' |  | 171.0 | na | na |
| 16 | CH$_2$ | 41.8 | 4.38 (m) | nd |
| 16' |  | 42.0 | 4.38 (m) | nd |
| 17 | C | 144.7 | na | na |
| 18 | CH | 127.5 | 7.44 (d) | 8.2 |
|  |  | 127.6 | 7.44 | nd |
| 19 | CH | 127.8 | 7.66 (d) | 8.2 |
| 20 | C | 125.1 | na | na |
| 21 | C | 157.9 | na | na |
| 24 | CH$_3$ | 63.3 | 3.83 (s) | na |
| 24' |  | 63.3 | 3.82 (s) | na |
| 26 | CH$_2$ | 51.4 | 2.41 (m) | nd |
| 27 | CH$_2$ | 27.3 | 1.52 (m) | nd |
| 28 | CH$_2$ | 21.7 | 1.30 (m) | nd |
| 29 | CH$_3$ | 14.0 | 0.83 (t) | 7.3 |

$^a$Relative to the solvent resonance at 49.0 ppm.
$^b$Relative to the solvent resonance at 3.30 ppm.
$^c$s = singlet, d = doublet, dd = doublet of doublets, t = triplet, m = multiplet.
$^d$The resonance is a triplet due to coupling with the two fluorine nuclei F1. $^1J_{CF}$ = 258 Hz.
$^e$The $^4J_{HH}$ coupling with the meta-protons is not fully resolved.
na = not applicable,
nd = not determined HRMS calculated for $C_{26}H_{32}ClF_2N_4O_8S$ (M−H)$^-$ 633.1597, found 633.1600.

Crystals of Compound A n-butanesulfonic acid salt (obtained as described above in Method 17-B) were analyzed by XRPD and the results are tabulated below (Table 9) and are shown in FIG. 4.

TABLE 9

| d-value (Å) | Intensity (%) | Intensity |
|---|---|---|
| 14.3 | 8 | m |
| 12.8 | 81 | vs |
| 10.3 | 44 | s |
| 8.2 | 4 | w |
| 7.7 | 13 | m |

TABLE 9-continued

| d-value (Å) | Intensity (%) | Intensity |
|---|---|---|
| 6.7 | 2 | vw |
| 6.4 | 8 | m |
| 6.2 | 18 | m |
| 6.0 | 100 | vs |
| 5.8 | 29 | s |
| 5.6 | 4 | w |
| 5.4 | 11 | m |
| 5.3 | 16 | m |
| 5.1 | 15 | m |
| 4.98 | 6.5 | w |
| 4.91 | 34 | s |
| 4.76 | 56 | s |
| 4.57 | 20 | m |
| 4.42 | 13 | m |
| 4.36 | 19 | m |
| 4.30 | 45 | s |
| 4.18 | 42 | s |
| 4.13 | 88 | vs |
| 4.01 | 34 | s |
| 3.92 | 28 | s |
| 3.82 | 18 | m |
| 3.64 | 6.6 | w |
| 3.58 | 16 | m |
| 3.47 | 5 | w |
| 3.44 | 6 | w |
| 3.38 | 12 | m |
| 3.35 | 32 | s |
| 3.32 | 22 | s |
| 3.29 | 12 | m |
| 3.20 | 8 | m |
| 3.17 | 9 | m |
| 3.02 | 12 | m |
| 2.90 | 6 | w |
| 2.81 | 3.9 | vw |
| 2.75 | 3 | vw |
| 2.64 | 3.5 | vw |
| 2.59 | 10 | m |
| 2.57 | 8 | m |
| 2.50 | 4 | w |
| 2.45 | 5 | w |
| 2.40 | 6 | w |
| 2.31 | 3 | vw |

DSC showed an endotherm with an extrapolated melting onset temperature of ca 118° C. and TGA showed a 0.04% weight loss.

Method 18: Preparation of Salts of Compound B

Method 18-A: General Method for Salt Preparation

The following generic method was employed to prepare salts of Compound B: 200 mg of compound B (see Preparation B above) was dissolved in 5 mL of MIBK (methyl isobutyl ketone). To this solution was added a solution of the relevant acid (1.0 or 0.5 molar equivalent, as indicated in Table 10) dissolved in 1.0 mL of MIBK. After stirring for 10 minutes at room temperature, the solvent was removed by way of a rotary evaporator. The remaining solid material was re-dissolved in about 8 mL of acetonitrile:H$_2$0 (1:1). Freeze-drying afforded colorless amorphous material in each case.

Acid Employed:
Esylate (ethanesulfonic acid)
Besylate (benzene sulfonic acid)
Cyclohexylsulphamate
Sulphate
Bromide
p-Toluenesulphonate
2-Naphtalenesulfonate
Hemisulfate Methanesulphonate
Nitrate
Hydrochloride Appropriate characterising data are shown in Table 10

TABLE 10

| Salt | Mw acid | Mw salt | MS ES− |
|---|---|---|---|
| Esylate | 110.13 | 643.01 | 108.8 |
|  |  |  | 531.1 |
|  |  |  | 641.0 |
| Besylate | 158.18 | 691.06 | 156.8 |
|  |  |  | 531.1 |
|  |  |  | 689.2 |
| Cyclohexylsulphamate | 179.24 | 712.12 | 177.9 |
|  |  |  | 531.2 |
|  |  |  | 710.4 |
| Sulphate | 98.08 | 630.96 | 531.1 |
| Bromide | 80.91 | 613.79 | 531.2 |
|  |  |  | 613.1 |
| p-Toluenesulphonate | 172.20 | 705.08 | 170.9 |
|  |  |  | 531.1 |
|  |  |  | 703.1 |
| 2-Naphtalenesulfonate | 208.24 | 741.12 | 206.9 |
|  |  |  | 531.1 |
|  |  |  | 739.3 |
| Hemisulfate | 98.07 | 1163.8 (1:2) | 531.1 |
|  |  | 630.85 (1:1) | 631.0 |
| Methanesulphonate | 96.11 | 628.99 | 531.1 |
|  |  |  | 627.1 |
| Nitrate | 63.01 | 595.89 | 531.0 |
|  |  |  | 594.0 |
| Hydrochloride | 36.46 | 569.34 | 531.0 |
|  |  |  | 569.0 |

All salts formed in this Example were amorphous.

Method 18-B

Further amorphous salts of Compound B were made using analogous techniques to those described in Method 18-A above for the following acids:
1,2-Ethanedisulfonic (0.5 salt)
1S-Camphorsulfonic
(+/−)-Camphorsulfonic
p-Xylenesulfonic
2-Mesitylenesulfonic
Saccharin
Maleic
Phosphoric
D-glutamic
L-arginine
L-lysine
L-lysine*HCl Method 18-C: Preparation of Amorphous Compound B, hemi-1,5-naphtalenedisulfonic acid salt Amorphous Compound B (110.9 mg) was dissolved in 2.5 mL 2-propanol and 0.5 equivalent of 1,5-naphthalene-disulfonic acid tetrahydrate was added (dissolved in 1 mL 2-propanol). The sample was stirred overnight. Only small particles (amorphous) or oil drops were observed by microscopy. The sample was evaporated to dryness.

Method 18-D: Preparation of Crystalline Compound B, hemi-1,5-naphtalenedisulfonic acid salt The crystallization experiment was carried out at ambient temperature. Amorphous Compound B (0.4 gram) was dissolved in ethanol (1.5 mL) and 0.5 eq of 1,5-naphthalene-disulfonic acid tetrahydrate (1.35 gram, 10% in ethanol) was added. Heptane (0.7 mL) was then added until the solution became slightly cloudy. After about 15 minutes the solution became turbid. After about 30 minutes thin slurry was obtained and additional heptane (1.3 mL) was added. The slurry was than left overnight for ripening. To dilute the thick slurry, a mixture of ethanol and heptane (1.5 mL and 1.0 mL respectively) was added. After about 1 hour the slurry was filtered and the crystals were washed with a mixture of ethanol and heptane (1.5:1) and finally with pure heptane. The crystals were dried at ambient temperature in 1 day. The dry crystals weighed 0.395 g.

Method 18-E: Preparation of Crystalline Compound B, hemi-1,5-naphtalenedisulfonic acid salt Amorphous Compound B (1.009 gr) was dissolved in 20 mL 2-propanol+20 mL ethyl acetate. 351.7 mg 1,5-naphtalene-disulfonic acid tetrahydrate, dissolved in 20 mL 2-propanol, was added drop by drop. Precipitation occurred in about 5 minutes. The slurry was stirred over night and then filtered.

Method 18-F: Preparation of Crystalline Compound B, hemi-1,5-naphtalenedisulfonic acid salt 430.7 mg of the 1,5-naphtalene-disulfonic acid salt was dissolved in 30 mL 1-propanol. The solution was heated to boiling in order to dissolve the substance. The solution was left over night at ambient temperature for crystallization and then the crystals were filtered off.

Method 18-G: Preparation of Crystalline Compound B, hemi-1,5-naphtalenedisulfonic acid salt The mother liquid from Method 18-F was evaporated and the solid rest (61.2 mg) was dissolved in 6 mL acetonitrile/1-propanol, ratio 2:1. The solution was left overnight at ambient temperature to crystallize and then the crystals were filtered off.

Method 18-H: Preparation of Crystalline Compound B, hemi-1,5-naphtalenedisulfonic acid salt The sample from Method 18-C was dissolved in about 2 mL methanol. Ethanol (about 3 mL) was added as anti-solvent at ambient temperature and seeds were added. No crystallization occurred, so solvents were evaporated (about half of the amount) and a new portion of ethanol (about 2 mL) and seeds were added. Crystalline particles were formed when stirred at ambient temperature during night.

Method 18-I: Preparation of Crystalline Compound B, hemi-1,5-naphtalenedisulfonic acid salt Amorphous Compound B (104.1 mg) was dissolved in 2-propanol and 1 equivalent of 1,5-naphthalene-disulfonic acid tetrahydrate, dissolved in 2-propanol, was added In total, the 2-propanol amount was about 2.5 mL. The solution was stirred at 44° C. for about 80 minutes and a precipitate was formed. The particles were crystalline according to polarised light microscopy. The sample was filtered.

Method 18-J: Preparation of Crystalline Compound B, hemi-1,5-naphtalenedisulfonic acid salt Compound B, hemi-1,5-naphtalenedisulfonic acid salt (56.4 mg) was dissolved in 1.5 mL methanol. Methyl ethyl ketone (3 mL) was added. Seeds were added to the solution and crystallization started. The crystals were filtered off, washed with methyl ethyl ketone and air dried.

Method 18-K: Preparation of crystalline Compound B, hemi-1,5-naphtalenedisulfonic acid salt Amorphous Compound B (161.0 mg) was dissolved in 3.5 mL 1-Butanol and the solution was heated to 40° C. In another beaker 57.4 mg of naphthalene-disulfonic acid tetrahydrate was dissolved in 3 mL 1-Butanol. A couple of drops of the acid solution were added to the solution of compound B. Then seeds were added to the solution and after 2 hours the rest of the acid solution was added (at 40° C.) slowly. Then the temperature was slowly decreased to room temperature and the experiment was left under stirring overnight. The slurry was filtered, washed with 1-Butanol and dried under vacuum at 44° C. for 2 hours. The yield was 83%.

Characterisation

Crystals of Compound B, hemi-1,5-naphtalenedisulfonic acid salt, obtained by way of Method 18-D above, was characterised by NMR as follows: 21.3 mg of the salt was dissolved in deuterated methanol, 0.7 ml was investigated with NMR spectroscopy. A combination of 1D ($^1$H, $^{13}$C and selective NOE) and 2D (gCOSY, gHSQC and gHMBC) NMR experiments was used. All data are in good agreement with the proposed structure, shown below. All carbons and the protons attached to carbons are assigned. Protons attached to heteroatoms are exchanged for deuterium from the solvent and are not detected. Most resonances in the 1D $^1$H and $^{13}$C NMR spectra are present as sets of two peaks. The reason for this is a slow rotation around the C9-N10 bond, which results in two atropisomers that simultaneously exist in the solution. The 1D NOE experiment is an evidence for this. When a resonance of one atropisomer is irradiated, the saturation is transferred to the corresponding peak of the other atropisomer. The resonances corresponding to the 1,5-naphtalenedisulfonate counter ion do not show atropisomerism.

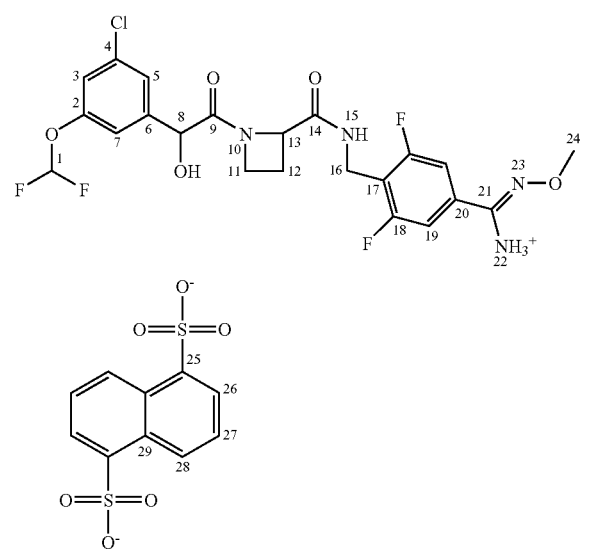

There are four fluorine atoms in the molecule. They give rise to split resonances for some protons and carbons. Both the proton and the carbon resonance corresponding to position 1 are split due to the spincoupling with the two fluorine nuclei in that position. The coupling constants are $^2J_{HF}$=73 Hz and $^1J_{CF}$=263 Hz. Further, the proton resonance corresponding to H19 is a distorted doublet with $^3J_{HF}$=6.9 Hz due to the spincoupling with the fluorine nuclei in position 18. Carbon resonances corresponding to C17, C18, C19 and C20 also exhibit couplings with these fluorine nuclei. The C17 and C20 resonances are triplets with $^2J_{CF}$=19 Hz and $^3J_{CF}$=11 Hz, respectively. The C18 resonance is a doublet of doublets with coupling constants $^1J_{CF}$=251 Hz and $^3J_{CF}$=8 Hz. The C19 resonance is a multiplet.

Comparing the magnitudes of integrals for resonances corresponding to the 1,5-naphtalenedisulfonate counter ion and the mother compound gives the stoichiometric relation of a single 1,5-naphtalenedisulfonate counter ion crystallized with two molecules of the mother compound.

$^1$H and $^{13}$C NMR chemical shift assignment and proton-proton correlations are shown in Table 11.

TABLE 11

| Atom No. | Type | $^{13}$C shift/ ppm$^a$ | $^1$H shift/ppm$^b$ and multiplicity$^c$ | $J_{HH}$/Hz | Through-bond correlation to $^1$H$^d$ |
|---|---|---|---|---|---|
| 1 | CHF$_2$ | 117.5$^e$ | 6.91 (t) | 73 ($^2J_{HF}$) | nd |
| 1' | | 117.5$^e$ | 6.87 (t) | 73 ($^2J_{HF}$) | nd |
| 2 | C | 153.5 | na | na | na |
| 2' | | 153.3 | na | na | na |
| 3 | CH | 120.0 | 7.14 (t)$^n$ | nd | 5, 7 |
| 3' | | 119.6 | 7.11 (t)$^n$ | nd | 5', 7' |
| 4 | C | 136.1 | na | na | na |
| 4' | | 135.8 | na | na | na |
| 5 | CH | 125.0 | 7.31 (t)$^n$ | nd | 3, 7 |
| 5' | | 124.9 | 7.28 (t)$^n$ | nd | 3', 7' |
| 6 | C | 144.4 | na | na | na |
| 6' | | 145.3 | na | na | na |
| 7 | CH | 117.2 | 7.16 (t)$^n$ | nd | 3, 5 |
| 7' | | 117.1 | 7.12 (t)$^n$ | nd | 3', 5' |
| 8 | CH | 72.9 | 5.15 (s) | na | nd |
| 8' | | 73.6 | 5.07 (s) | na | nd |
| 9 | CO | 173.0 | na | na | na |
| 9' | | 173.5 | na | na | na |
| 11 | CH$_2$ | 51.5 | a: 4.29 (m) b: 4.13 (m) | nd | 12, 13 |
| 11' | | 48.6 | a: 4.01 (m) b: 3.93 (m) | nd | 12', 13' |
| 12 | CH$_2$ | 21.7 | a: 2.46 (m) b: 2.17 (m) | nd | 11, 13 |
| 12' | | 22.8 | a: 2.61 (m) b: 2.03 (m) | nd | 11', 13' |
| 13 | CH | 62.8 | 4.70 (dd) | 6.0 and 9.4 | 12 |
| 13' | | 65.8 | 5.14 (dd) | 5.6 and 9.1 | 12' |
| 14 | CO | 172.4 | na | na | na |
| 14' | | 173.2 | na | na | na |
| 16 | CH$_2$ | 32.3 | 4.51 (m) | nd | nd |
| 16' | | 32.5 | 4.51 (m) | nd | nd |
| 17 | C | 121.0$^f$ | na | na | na |
| 18 | CF | 162.8$^g$ | na | na | na |
| 19 | CH | 112.7$^i$ | 7.35 (d) | 6.9 ($^3J_{HF}$) | nd |
| 20 | C | 127.9$^k$ | na | na | na |
| 21 | C | 160.0 | na | na | na |
| 21' | | 159.9 | na | na | na |
| 24 | CH$_3$ | 64.8 | 3.93 (s) | na | nd |
| 24' | | 64.8 | 3.92 (s) | na | nd |
| 25 | C | 142.4 | na | na | na |
| 26 | CH | 126.8 | 8.16 (d) | 7.2 | 27, 28 |
| 27 | CH | 125.9 | 7.54 (dd) | 8.6 and 7.2 | 26, 28 |

TABLE 11-continued

| Atom No. | Type | $^{13}$C shift/ ppm$^a$ | $^1$H shift/ppm$^b$ and multiplicity$^c$ | $J_{HH}$/Hz | Through-bond correlation to $^1$H$^d$ |
|---|---|---|---|---|---|
| 28 | CH | 131.0 | 8.97 (d) | 8.6 | 26, 27 |
| 29 | C | 131.1 | na | na | na |

$^a$Relative to the solvent resonance at 49.0 ppm.
$^b$Relative to the solvent resonance at 3.30 ppm.
$^c$s = singlet, d = doublet, dd = doublet of doublets, t = triplet, m = multiplet.
$^d$Obtained in the gCOSY experiment.
$^e$The resonance is a triplet due to coupling with the two fluorine nuclei F1. $^1J_{CF}$ = 263 Hz.
$^f$The resonance is a triplet due to coupling to the two fluorine nuclei F18. $^2J_{CF}$ = 19 Hz.
$^g$The resonance is a doublet of doublets due to coupling to the two fluorine nuclei F18. $^1J_{CF}$ = 251 Hz and $^3J_{CF}$ = 8 Hz.
$^j$The resonance is a multiplet due to coupling to the two fluorine nuclei F18.
$^k$The resonance is a triplet due to coupling to the two fluorine nuclei F18. $^3J_{CF}$ = 11 Hz.
$^m$The $^4J_{HH}$ coupling with the meta-protons is not fully resolved.
na = not applicable,
nd = not determined Crystals of Compound B, hemi-1,5-naphtalenedisulfonic acid salt (obtained by way of Method 18-I above, were analyzed by XRPD and the results are tabulated below (Table 12) and are shown in FIG. 5.

TABLE 12

| d value (Å) | Intensity (%) | Intensity |
|---|---|---|
| 18.3 | 99 | vs |
| 12.5 | 22 | s |
| 9.9 | 22 | s |
| 9.1 | 67 | vs |
| 8.0 | 18 | m |
| 7.5 | 17 | m |
| 6.8 | 37 | s |
| 6.7 | 59 | s |
| 6.1 | 39 | s |
| 6.0 | 21 | s |
| 5.6 | 66 | vs |
| 5.5 | 98 | vs |
| 4.94 | 48 | s |
| 4.56 | 59 | s |
| 4.39 | 35 | s |
| 4.27 | 33 | s |
| 4.13 | 81 | vs |
| 4.02 | 87 | vs |
| 3.86 | 88 | vs |
| 3.69 | 69 | vs |
| 3.63 | 100 | vs |
| 3.57 | 49 | s |
| 3.48 | 53 | s |
| 3.23 | 35 | s |
| 3.19 | 43 | s |
| 3.16 | 38 | s |

DSC showed an endotherm with an extrapolated melting onset temperature of ca 183° C. and TGA showed a 0.3% weight loss between 25-110° C.

ABBREVIATIONS

Ac=acetyl
APCI=atmospheric pressure chemical ionisation (in relation to MS)
API=atmospheric pressure ionisation (in relation to MS)
aq.=aqueous
Aze(& (S)-Aze)=(S)-azetidine-2-carboxylate (unless otherwise specified)
Boc=tert-butyloxycarbonyl
br=broad (in relation to NMR)
CI=chemical ionisation (in relation to MS)
d=day(s)
d=doublet (in relation to NMR)
DCC=dicyclohexyl carbodiimide
dd=doublet of doublets (in relation to NMR)
DIBAL-H=di-isobutylaluminum hydride
DIPEA=diisopropylethylamine
DMAP=4-(N,N-dimethylamino) pyridine
DMF=N,N-dimethylformamide
DMSO=dimethylsulfoxide
DSC=differential scanning colorimetry
DVT=deep vein thrombosis
EDC=1-(3-dimethylaminopropyl)-3-ethylcarbodiimide hydrochloride
eq.=equivalents
ES=electrospray
ESI=electrospray interface
Et=ethyl
ether=diethyl ether
EtOAc=ethyl acetate
EtOH=ethanol
Et$_2$O=diethyl ether
HATU=O-(azabenzotriazol-1-yl)-N,N,N',N'-tetramethyluronium hexafluorophosphate
HBTU=[N,N,N',N'-tetramethyl-O-(benzotriazol-1-yl)uronium hexafluorophosphate]
HCl=hydrochloric acid, hydrogen chloride gas or hydrochloride salt (depending on context)
Hex=hexanes
HOAc=acetic acid
HPLC=high performance liquid chromatography
LC=liquid chromatography
m=multiplet (in relation to NMR)
Me=methyl
MeOH=methanol
min.=minute(s)
MS=mass spectroscopy
MTBE.=methyl tert-butyl ether
NMR=nuclear magnetic resonance
OAc=acetate
Pab=para-amidinobenzylamino
H-Pab=para-amidinobenzylamine
Pd/C=palladium on carbon
Ph=phenyl
PyBOP=(benzotriazol-1-yloxy)tripyrrolidinophosphonium hexafluorophosphate
q=quartet (in relation to NMR)
QF=tetrabutylammonium fluoride
rt/RT=room temperature
s=singlet (in relation to NMR)
t=triplet (in relation to NMR)
TBTU=[N,N,N',N'-tetramethyl-O-(benzotriazol-1-yl)uronium tetrafluoroborate]
TEA=triethylamine
Teoc=2-(trimethylsilyl)ethoxycarbonyl
TEMPO=2,2,6,6-tetramethyl-1-piperidinyloxy free radical
TFA=trifluoroacetic acid
TGA=thermogravimetric analysis
THF=tetrahydrofuran
TLC=thin layer chromatography
UV=ultraviolet Prefixes n-, s-, i-, t- and tert- have their usual meanings: normal, secondary, iso, and tertiary.

The invention is illustrated, but in no way limited, by the following Examples. Unless otherwise specified, HPMC polymers were obtained from Shin-Etsu (trademark METOLOSE™). For iota-carrageenan the supplier was Fluka for all Examples except Examples 11 and 12 (when CP-Kelco was the supplier). Specific grades and their USP equivalents are indicated below (once only, on the first occasion that they are disclosed).

General Test Method

Three individual tablets were tested for drug release in 900 ml media using a USP dissolution apparatus 2 (paddle+basket[1]) at 50 rpm and 37° C. The dissolution media used were 0.1 M hydrochloric acid (pH 1) and 0.1 M sodium phosphate buffer (pH 6.8). In-line quantitation was performed using the C Technologies fibre optic system with 220 nm as the analytical wavelength when 0.1 M HCl was used as the dissolution media and with 260 nm as the analytical wavelength when phosphate buffer pH 6.8 was used as the dissolution media. 350 nm was used as the reference wavelength with both media. For the first two hours of the analysis the release value was measured every 15 minutes, and then every hour for the remainder of the analysis.

[1 A custom made quadrangular basket of mesh wire, soldered in one of its upper, narrow sides to the end of a steel rod. The rod is brought through the cover of the dissolution vessel and fixed by means of two Teflon nuts, 3.2 cm from the centre of the vessel. The lower edge of the bottom of the basket is adjusted to be 1 cm above the paddle. The basket is directed along the flow stream with the tablet under test standing on its edge].

EXAMPLE 1

Direct compression of Compound A with HPMC 10 000 cps and HPMC 50 cps, ratio 50:50.

The active substance and excipients material were mixed in a beeting vat. The granulate was lubricated with sodium stearyl fumarate and compressed into tablets using an excenterpress.

|  | Weight | Amount |
| --- | --- | --- |
| Compound A | 50.5 mg | 20.0% |
| HPMC 10 000 cPs | 100.0 mg | 39.5% |
| HPMC 50 cPs | 100.0 mg | 39.5% |
| Sodium stearyl fumarate | 2.5 mg | 1.0% |

| Release Data | | |
| --- | --- | --- |
| Time (min) | % released in buffer pH 1.1 | % released in buffer pH 6.8 |
| 0 | 0 | 0 |
| 15 | 7 | 1 |
| 30 | 11 | 2 |
| 45 | 14 | 3 |
| 60 | 17 | 4 |
| 120 | 27 | 7 |
| 180 | 35 | 10 |
| 240 | 42 | 13 |
| 360 | 55 | 18 |
| 480 | 65 | 23 |
| 600 | 74 | 28 |
| 720 | 81 | 33 |
| 840 | 86 | 38 |
| 960 | 93 | 43 |
| 1080 | 99 | 47 |
| 1200 | 105 | 52 |

EXAMPLE 2

Granulation and compression of Compound A with HPMC, Solubilizing Agent and fillers.

The active substance, antioxidant and solubilizer were dissolved in ethanol and distributed in the excipients. This mixture was then granulated with HPC dissolved in ethanol. The granules were then dried in a drying oven. The granulate was lubricated with sodium stearyl fumarate and compressed into tablets using an excenterpress.

|  | Weight | Amount |
| --- | --- | --- |
| Compound A | 10 mg | 4.7% |
| Polyoxyl 40 hydrogenated castor oil | 10 mg | 4.7% |
| Propyl gallate | 0.06 mg | 0.03% |
| HPC LF | 10 mg | 4.7% |
| HPMC 50 cPs | 70 mg | 33% |
| HPMC 10 000 cPs | 30 mg | 14% |
| Sodium aluminium silicate | 47 mg | 22% |
| Lactose, anhydrous | 28 mg | 13% |
| Microcrystalline cellulose | 3 mg | 1.4% |
| Sodium stearyl fumarate | 4 mg | 2.0% |

| Release Data | | |
| --- | --- | --- |
| Time (min) | % released in buffer pH 1.1 | % released in buffer pH 6.8 |
| 0 | 0 | 0 |
| 15 | 10 | 8 |
| 30 | 15 | 10 |
| 45 | 20 | 13 |
| 60 | 24 | 16 |
| 120 | 39 | 26 |
| 180 | 52 | 36 |
| 240 | 64 | 45 |
| 360 | 83 | 65 |
| 480 | 98 | 84 |
| 600 | 108 | 98 |
| 720 | 111 | 114 |
| 840 | 113 | 123 |
| 960 | 114 | 129 |
| 1080 | 117 | 132 |
| 1200 | 120 | 132 |

The results have not been corrected for the significant background absorption from the tablet matrix, thus release values of 120% and 132% are seen in 0.1 M HCl and 0.1 M sodium phosphate buffer pH 6.8, respectively.

EXAMPLE 3

Granulation and compression of Compound A with HPMC, SDS and Fillers.

The active substance and excipients material were mixed in a beeting vat. The granulate was lubricated with sodium-stearylfumarate and compressed into tablets using an excenterpress.

|  | Weight | Amount |
| --- | --- | --- |
| Compound A | 50 mg | 23% |
| HPC LF | 13 mg | 6% |
| HPMC 50 cPs | 100 mg | 47% |
| Mannitol | 50 mg | 23% |
| Sodium lauryl sulfate | 20 mg | 9% |
| Sodium dihydrogen phosphate dihydrate | 75 mg | 35% |
| Sodium stearyl fumarate | 3 mg | 1% |

EXAMPLE 4: An Example of a Formulation Comprising the Esylate Salt of Compound A, HPMC and SDS

|  | Weight | Amount |
| --- | --- | --- |
| esylate salt of Compound A | 50 mg | 23% |
| HPC LF | 13 mg | 6% |
| HPMC 50 cPs | 100 mg | 47% |
| Mannitol | 50 mg | 23% |
| Sodium lauryl sulfate | 20 mg | 9% |
| Sodium dihydrogen phosphate dihydrate | 75 mg | 35% |
| Sodium stearyl fumarate | 3 mg | 1% |

The formulation was prepared according to the method of Example 3.

EXAMPLE 5: An Example of a Formulation with Esylate Salt of Compound A and Xanthan Gum

|  | Weight | Amount |
| --- | --- | --- |
| esylate salt of Compound A | 50 mg | 19% |
| Xanthan Gum | 200 mg | 80% |
| Sodium stearyl fumarate | 2.5 mg | 1% |

The formulation was prepared according to the method of Example 3.

EXAMPLE 6: Example of a Formulation of the Esylate Salt of Compound A with HPMC and iota-Carregeenan

|  | Weight | Amount |
| --- | --- | --- |
| esylate salt of Compound A | 500 mg | 50% |
| HPMC 10 000 cPs | 245 mg | 25% |
| Iota-Carrageenan | 245 mg | 25% |
| Sodium stearyl fumarate | 10 mg | 1% |

The formulation was prepared according to the method of Example 3.

EXAMPLE 7: Example of a Formulation of the n-Propyl Sulphonic Acid Salt of Compound A with HPMC and iota-Carregeenan

|  | Weight | Amount |
| --- | --- | --- |
| n-propyl sulphonic acid salt of Compound A | 100 mg | 20% |
| HPMC 10 000 cPs | 150 mg | 30% |
| Iota-Carrageenan | 250 mg | 50% |
| Sodium stearyl fumarate | 5 mg | 1% |

The formulation was prepared according to the method of Example 3.

EXAMPLE 8: Example of a Formulation of the Besylate Salt of Compound A with HPMC and iota-Carregeenan

|  | Weight | Amount |
| --- | --- | --- |
| besylate salt of Compound A | 20 mg | 16% |
| HPMC 10 000 cPs | 50 mg | 41% |
| Iota-Carrageenan | 50 mg | 41% |
| Sodium stearyl fumarate | 2 mg | 2% |

The formulation was prepared according to the method of Example 3.

EXAMPLE 9

Direct compression of esylate salt of Compound A with HPMC 10 000 cPs and HPMC 50 cPs, Ratio 50:50.

|  | Weight | Amount |
| --- | --- | --- |
| esylate salt of Compound A | 50.5 mg | 20.0% |
| HPMC 10 000 cPs | 100.0 mg | 39.5% |
| HPMC 50 cPs | 100.0 mg | 39.5% |
| Sodium stearyl fumarate | 2.5 mg | 1.0% |

The active substance and excipients material has been mixed in a beeting vat. The granulate was lubricated with sodium stearyl fumarate and compressed into tablets using an excenterpress.

| | Release Data | |
| --- | --- | --- |
| Time (min) | % released in buffer pH 1.1 | % released in buffer pH 6.8 |
| 0 | 0 | 0 |
| 15 | 6 | 2 |
| 30 | 10 | 4 |
| 45 | 13 | 5 |
| 60 | 15 | 6 |
| 120 | 23 | 9 |
| 180 | 30 | 12 |
| 240 | 37 | 15 |
| 360 | 48 | 20 |
| 480 | 57 | 25 |
| 600 | 65 | 30 |
| 720 | 72 | 34 |
| 840 | 78 | 38 |
| 960 | 83 | 42 |
| 1080 | 87 | 46 |
| 1200 | 90 | 49 |

EXAMPLE 10

Direct compression of esylate salt of Compound A with HPMC 10 000 cPs and iota-Carrageenan, Ratio 50:50.

The active substance and excipients material has been mixed in a beeting vat. The granulate was lubricated with sodiumstearylfumarate and compressed into tablets using an excenterpress.

|                          | Weight   | Amount |
|--------------------------|----------|--------|
| esylate salt of Compound A | 50.5 mg  | 20.0%  |
| HPMC 10 000 cPs          | 100.0 mg | 39.5%  |
| Iota-carrageenan (Fluka) | 100.0 mg | 39.5%  |
| Sodium stearyl fumarate  | 2.5 mg   | 1.0%   |

Release Data

| Time (min) | % released in buffer pH 1.1 | % released in buffer pH 6.8 |
|------------|------------------------------|------------------------------|
| 0    | 0  | 0   |
| 15   | 3  | 2   |
| 30   | 5  | 3   |
| 45   | 6  | 5   |
| 60   | 8  | 6   |
| 120  | 15 | 13  |
| 180  | 22 | 21  |
| 240  | 29 | 30  |
| 360  | 43 | 51  |
| 480  | 57 | 72  |
| 600  | 70 | 91  |
| 720  | 81 | 104 |
| 840  | 88 | 106 |
| 960  | 94 | 106 |
| 1080 | 96 | 106 |
| 1200 | 96 | 106 |

EXAMPLE 11

The besylate salt of Compound A and excipient materials were granulated in a high shear granulator. The granulate was dried and lubricated with sodiumstearylfumarate and compressed into tablets using an excenterpress.

|                           | Weight  | Amount |
|---------------------------|---------|--------|
| Besylate salt of Compound A | 230 mg  | 57%    |
| HPMC 10 000 cPs           | 17 mg   | 4%     |
| HPMC 50 cPs               | 12 mg   | 3%     |
| Iota-Carrageenan          | 141 mg  | 35%    |
| Sodium stearyl fumarate   | 4 mg    | 1%     |

Release Data

| Time (hours) | % released in buffer pH 1.1 | % released in buffer pH 6.8 |
|--------------|------------------------------|------------------------------|
| 0    | 0  | 0  |
| 0.5  | 6  | 5  |
| 1    | 10 | 12 |
| 1.5  | 14 | 20 |
| 2    | 19 | 28 |
| 3    | 27 | 45 |
| 4    | 35 | 61 |
| 5    | 42 | 76 |
| 6    | —  | 87 |
| 7    | —  | 95 |
| 8    | —  | 98 |
| 9    | —  | 98 |
| 10   | —  | 98 |
| 12   | —  | 98 |

EXAMPLE 12

The besylate salt of Compound A and excipient materials were granulated in a high shear granulator. The granulate was dried and lubricated with sodiumstearylfumarate and compressed into tablets using an excenterpress.

|                           | Weight  | Amount |
|---------------------------|---------|--------|
| Besylate salt of Compound A | 230 mg  | 45%    |
| HPMC 10 000 cPs           | 14 mg   | 3%     |
| HPMC 50 cPs               | 163 mg  | 32%    |
| Iota-Carrageenan          | 94 mg   | 19%    |
| Sodium stearyl fumarate   | 5 mg    | 1%     |

Release Data

| Time (hours) | % released in buffer pH 1.1 | % released in buffer pH 6.8 |
|--------------|------------------------------|------------------------------|
| 0    | 0  | 0   |
| 0.5  | 5  | 4   |
| 1    | 10 | 8   |
| 1.5  | 16 | 12  |
| 2    | 21 | 16  |
| 3    | 32 | 24  |
| 4    | 43 | 32  |
| 5    | 54 | 39  |
| 6    | —  | 46  |
| 7    | —  | 53  |
| 8    | —  | 60  |
| 9    | —  | 66  |
| 10   | —  | 71  |
| 12   | —  | 81  |
| 14   | —  | 88  |
| 16   | —  | 94  |
| 18   | —  | 98  |
| 20   | —  | 100 |

EXAMPLE 13

The besylate salt of Compound A and excipient materials were directly compressed.

|                           | Weight  | Amount |
|---------------------------|---------|--------|
| Besylate salt of Compound A | 263 mg  | 65%    |
| HPMC 50 cPs               | 137 mg  | 34%    |
| Sodium stearyl fumarate   | 4 mg    | 1%     |

Release Data

| Time (min) | % released in buffer pH 1.1 | % released in buffer pH 6.8 |
|------------|------------------------------|------------------------------|
| 0   | 0  | 0  |
| 15  | 3  | 4  |
| 30  | 8  | 7  |
| 45  | 13 | 10 |
| 60  | 18 | 14 |
| 75  | 23 | 17 |
| 90  | 27 | 20 |
| 105 | 32 | 23 |
| 120 | 36 | 26 |
| 150 | 44 | 32 |

-continued

Release Data

| Time (min) | % released in buffer pH 1.1 | % released in buffer pH 6.8 |
|---|---|---|
| 180 | 51 | 37 |
| 210 | 59 | 42 |
| 240 | 66 | 47 |
| 270 | 72 | 52 |
| 300 | 78 | 56 |
| 330 | — | 60 |
| 360 | — | 64 |
| 390 | — | 67 |
| 420 | — | 70 |
| 450 | — | 74 |
| 480 | — | 76 |
| 510 | — | 79 |
| 540 | — | 82 |
| 570 | — | 84 |
| 600 | — | 86 |

EXAMPLE 14

Examples of formulations comprising the besylate salt of Compound A. Examples 14-A and 14-B are prepared according to the general method of Example 3 or 11.

EXAMPLE 14-A

| | Weight | Amount |
|---|---|---|
| Besylate salt of Compound A | 50 mg | 23% |
| HPC LF | 13 mg | 6% |
| HPMC 50 cPs | 100 mg | 47% |
| Mannitol | 50 mg | 23% |
| Sodium lauryl sulfate | 20 mg | 9% |
| Sodium dihydrogen phosphate dihydrate | 75 mg | 35% |
| Sodium stearyl fumarate | 3 mg | 1% |

EXAMPLE 14-B

| | Weight | Amount |
|---|---|---|
| Besylate salt of Compound A | 150 mg | 35% |
| PolyethylenoxideWSR N-60K | 200 mg | 47% |
| Microcrystalline cellulose | 60 | 14% |
| Polyvinyl pyrrolidone K30 | 10 mg | 2% |
| Sodium stearyl fumarate | 3 mg | 1% |

EXAMPLE 14-C

| | Weight | Amount |
|---|---|---|
| Besylate salt of Compound A | 132 mg | 30% |
| PolyethylenoxideWSR N-60K | 200 mg | 69% |
| Sodium stearyl fumarate | 4 mg | 1% |

The formulation was prepared according to the method of Example 3.

Release Data for Example 14-C

| Time (hours) | % released in buffer pH 6.8 |
|---|---|
| 0 | 0 |
| 0.5 | 3 |
| 1 | 5 |
| 1.5 | 7 |
| 2 | 9 |
| 2.5 | 11 |
| 3 | 13 |
| 4 | 18 |
| 5 | 23 |
| 6 | 28 |
| 7 | 33 |
| 8 | 38 |
| 9 | 44 |
| 10 | 49 |
| 11 | 54 |
| 12 | 60 |
| 13 | 65 |
| 14 | 70 |
| 15 | 74 |
| 16 | 78 |
| 17 | 82 |
| 18 | 86 |
| 19 | 89 |
| 20 | 92 |
| 21 | 95 |
| 22 | 97 |
| 23 | 99 |
| 24 | 100 |

EXAMPLE 15

Examples of formulations comprising the hemi-naphthalene 1,5-disulphonic acid salt of Compound B. All formulations are prepared according to the general method of Example 11.

EXAMPLE 15-A

| | Weight | Amount |
|---|---|---|
| Hemi-naphthalene 1,5-disulphonic acid salt of Compound B | 20 mg | 16% |
| HPMC 10 000 cPs | 50 mg | 41% |
| Iota-Carrageenan | 50 mg | 41% |
| Sodium stearyl fumarate | 2 mg | 2% |

EXAMPLE 15-B

| | Weight | Amount |
|---|---|---|
| Hemi-naphthalene 1,5-disulphonic acid salt of Compound B | 200 mg | 44% |
| PolyethylenoxideWSR N-60K | 250 mg | 55% |
| Sodium stearyl fumarate | 4 mg | 1% |

EXAMPLE 15-C

| | Weight | Amount |
|---|---|---|
| Hemi-naphthalene 1,5-disulphonic acid salt of Compound B | 200 mg | 40% |
| HPMC 10 000 cPs | 120 mg | 24% |
| HPMC 50 cPs | 180 mg | 36% |
| Sodium stearyl fumarate | 5 mg | 1% |

Further Examples may be prepared as above in which HPMC is replaced by, or mixed with, PEO. In case of a mixture, the proportion of PEO:HPMC may range from 90:10 to 10:90%. A particular mixture is PEO: HPMC 80%:20%, or 75%:25%.

EXAMPLE 16

Granulation and Compression of Compound A with HPMC, SDS and Fillers

The active substance and excipients material were mixed in a beeting vat. The granulate was lubricated with sodium-stearylfumarate and compressed into tablets using an excenterpress.

| | Weight | Amount |
|---|---|---|
| Compound A | 48 mg | 18% |
| HPC LF | 13 mg | 5% |
| HPMC 50 cPs | 60 mg | 22% |
| Mannitol | 50 mg | 19% |
| Sodium lauryl sulfate | 20 mg | 7% |
| Sodium dihydrogen phosphate dihydrate | 75 mg | 28% |
| Sodium stearyl fumarate | 3 mg | 1% |

| Release Data | | |
|---|---|---|
| Time (min) | % released in buffer pH 1.1 | % released in buffer pH 6.8 |
| 0 | 0 | 0 |
| 15 | 9 | 9 |
| 30 | 19 | 24 |
| 45 | 28 | 43 |
| 60 | 37 | 63 |
| 120 | 70 | 109 |
| 180 | 92 | 114 |
| 240 | 103 | 115 |
| 360 | 106 | 116 |
| 480 | 106 | 116 |
| 600 | 102 | 116 |
| 720 | 100 | 116 |
| 840 | 100 | 116 |
| 960 | 99 | 116 |
| 1080 | 99 | 116 |
| 1200 | 99 | 116 |

EXAMPLE 17

Direct Compression of Compound A with Xanthan Gum and iota-Carrageenan, Ratio 50:50

The active substance and excipients material were mixed in a beeting vat. The granulate was lubricated with sodium-stearylfumarate and compressed into tablets using an excenterpress.

| | Weight | Amount |
|---|---|---|
| Compound A | 50.5 mg | 20.0% |
| ι-Carrageenan | 100.0 mg | 39.5% |
| Xanthan Gum | 100.0 mg | 39.5% |
| Sodium stearyl fumarate | 2.5 mg | 1.0% |

| Release data | | |
|---|---|---|
| Time (min) | % released in buffer pH 1.1 | % released in buffer pH 6.8 |
| 0 | 0 | 0 |
| 15 | 2 | 1 |
| 30 | 4 | 1 |
| 45 | 5 | 2 |
| 60 | 7 | 3 |
| 120 | 12 | 6 |
| 180 | 16 | 11 |
| 240 | 21 | 17 |
| 360 | 30 | 31 |
| 480 | 39 | 45 |
| 600 | 48 | 60 |
| 720 | 56 | 75 |
| 840 | 63 | 88 |
| 960 | 70 | 97 |
| 1080 | 75 | 100 |
| 1200 | 79 | 100 |

Any Example above which uses the free base or a salt other than the besylate salt of Compound A may be repeated using the besylate salt of Compound A.

Particular aspects of the invention are provided as follows:
1. A modified release pharmaceutical composition comprising, as active ingredient, a compound of formula (I):

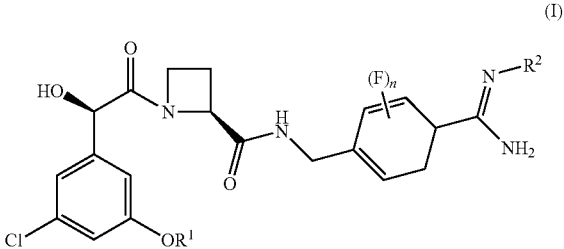

wherein
R$^1$ represents C$_{1-2}$ alkyl substituted by one or more fluoro substituents;
R$^2$ represents hydrogen, hydroxy, methoxy or ethoxy; and
n represents 0, 1 or 2;
or a pharmaceutically acceptable salt thereof; and a pharmaceutically acceptable diluent or carrier; provided that the formulation may only contain iota-carrageenan and a neutral gelling polymer when the compound of formula (I) is in the form of a salt.

2. A composition as described in aspect 1 wherein the active ingredient is a salt of:
Ph(3-Cl)(5-OCHF$_2$)—(R)CH(OH)C(O)—(S)Aze-Pab (OMe) (Compound A);
Ph(3-Cl)(5-OCHF$_2$)—(R)CH(OH)C(O)—(S)Aze-Pab(2,6-diF)(OMe) (Compound B); or,
Ph(3-Cl)(5-OCH$_2$CH$_2$F)—(R)CH(OH)C(O)—(S)Aze-Pab(OMe) (Compound C).

3 A composition as described in aspect 1 or 2 wherein the active ingredient is a crystalline salt of:
Ph(3-Cl)(5-OCHF$_2$)—(R)CH(OH)C(O)—(S)Aze-Pab(OMe) (Compound A);
Ph(3-Cl)(5-OCHF$_2$)—(R)CH(OH)C(O)—(S)Aze-Pab(2,6-diF)(OMe) (Compound B);
or, Ph(3-Cl)(5-OCH$_2$CH$_2$F)—(R)CH(OH)C(O)—(S)Aze-Pab(OMe) (Compound C).
4. A composition as described in aspect 1, 2 or 3 wherein the composition comprises a gelling matrix.
5. A composition as described in aspect 4 wherein the matrix comprises HPMC.
6. A composition as described in aspect 4 or 5 wherein the matrix comprises iota-carrageenan.
7. A composition as described in aspect 4 wherein the matrix comprises SDS.
8. A composition as described in aspect 2 and 5 or 2 and 6 wherein the matrix additionally comprises xanthan gum.
9. The use of a formulation as described in aspect 1 as a medicament.
10. The use of a formulation as described in aspect 1 in the manufacture of a medicament for the treatment of a cardiovascular disorder.
11. A method of treating a cardiovascular disorder in a patient suffering from, or at risk of, said disorder, which comprises administering to the patient a therapeutically effective amount of a pharmaceutical formulation as described in aspect 1.
12. A process for making an immediate release formulation as described in aspect 1.

Also provided is a composition obtainable by any of the Methods and/or Examples described herein.

The invention claimed is:

1. A modified release pharmaceutical composition comprising, as active ingredient, a compound of formula (I):

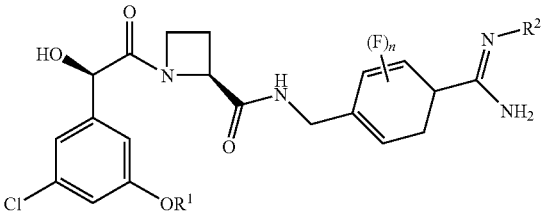

wherein
R$^1$ is CHF$_2$;
R$^2$ is methoxy; and
n is 0;
and one or more HPMCs and a lubricant wherein the compound of formula (I) is not in the form of a pharmaceutically acceptable salt.

2. A method of treating a cardiovascular disorder in a patient suffering from, or at risk of, said disorder, which comprises administering to the patient a therapeutically effective amount of a pharmaceutical composition as claimed in claim 1.

3. A method as claimed in claim 2 wherein the cardiovascular disorder is venous thrombosis, pulmonary embolism, arterial thrombosis, systemic embolism or atrial fibrillation.

4. A method as claimed in claim 2 wherein the cardiovascular disorder is atrial fibrillation.

5. A modified release pharmaceutical composition as claimed in claim 1 wherein the lubricant is sodium stearyl fumarate.

* * * * *